US005981200A

United States Patent [19]

Tsien et al.

[11] Patent Number: 5,981,200

[45] Date of Patent: *Nov. 9, 1999

[54] TANDEM FLUORESCENT PROTEIN CONSTRUCTS

[75] Inventors: Roger Y. Tsien, La Jolla; Roger Heim, Del Mar; Andrew Cubitt, San Diego, all of Calif.

[73] Assignees: The Regents of the University of California, Oakland, Calif.; Aurora Biosciences Corporation, La Jolla, Calif.

[ * ] Notice: This patent is subject to a terminal disclaimer.

[21] Appl. No.: 08/792,553

[22] Filed: Jan. 31, 1997

Related U.S. Application Data

[63] Continuation-in-part of application No. 08/594,575, Jan. 31, 1996.

[51] Int. Cl.[6] .................... G01N 33/573; G01N 33/53; G01N 33/52; C12N 15/62

[52] U.S. Cl. .................... 435/7.4; 435/7.72; 435/320.1; 435/325; 435/69.7; 435/183; 435/212; 530/350; 530/402; 536/23.4

[58] Field of Search .................... 435/6, 7.2, 7.21, 435/7.37, 7.4, 7.71, 7.72, 69.7, 183, 212, 252.3, 252.33, 320.1, 325; 530/350, 402; 536/23.4, 24.1; 930/280, 310

[56] References Cited

U.S. PATENT DOCUMENTS

| | | | |
|---|---|---|---|
| 4,314,936 | 2/1982 | Yaron et al. | 530/331 |
| 5,264,563 | 11/1993 | Huse | 536/25.3 |
| 5,491,084 | 2/1996 | Chalfie | 438/189 |
| 5,599,906 | 2/1997 | Dasmahapatra | 530/350 |
| 5,602,021 | 2/1997 | Davis et al. | 435/219 |
| 5,605,809 | 2/1997 | Komoriya et al. | 435/23 |
| 5,614,191 | 3/1997 | Puri et al. | 424/178.1 |
| 5,625,048 | 4/1997 | Tsien et al. | 536/23.4 |

FOREIGN PATENT DOCUMENTS

| | | |
|---|---|---|
| 0 428 000 A1 | 5/1991 | European Pat. Off. . |
| WO 91/01305 | 2/1991 | WIPO . |
| WO 94/28166 | 8/1994 | WIPO . |
| 94/28166 | 12/1994 | WIPO . |
| 94/28173 | 12/1994 | WIPO . |
| WO 95/07463 | 3/1995 | WIPO . |
| WO 95/21191 | 8/1995 | WIPO . |
| 96/13607 | 5/1996 | WIPO . |
| 96/23810 | 8/1996 | WIPO . |
| 96/23898 | 8/1996 | WIPO . |
| 96/27027 | 9/1996 | WIPO . |
| 96/27675 | 9/1996 | WIPO . |
| WO 97/11094 | 3/1997 | WIPO . |
| WO 97/28261 | 8/1997 | WIPO . |

*Primary Examiner*—Lila Feisee
*Assistant Examiner*—Michael Pak
*Attorney, Agent, or Firm*—Fish & Richardson P.C.

[57] ABSTRACT

This invention provides tandem fluorescent protein construct including a donor fluorescent protein moiety, an acceptor fluorescent protein moiety and a linker moiety that couples the donor and acceptor moieties. The donor and acceptor moieties exhibit fluorescence resonance energy transfer which is eliminated upon cleavage. The constructs are useful in enzymatic assays.

27 Claims, 10 Drawing Sheets

```
SEQ ID NO:1:
SEQ ID NO:2:

ATG AGT AAA GGA GAA GAA CTT TTC ACT GGA GTT GTC CCA ATT CTT GTT    48
Met Ser Lys Gly Glu Glu Leu Phe Thr Gly Val Val Pro Ile Leu Val
  1               5                  10

GAA TTA GAT GGT GAT GTT AAT GGG CAC AAA TTT TCT GTC AGT GGA GAG    96
Glu Leu Asp Gly Asp Val Asn Gly His Lys Phe Ser Val Ser Gly Glu
             20                  25          30

GGT GAA GGT GAT GCA ACA TAC GGA AAA CTT ACC CTT AAA TTT ATT TGC   144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT TTC   192
Thr Thr Gly Lys Leu Pro Val Pro Trp Pro Thr Leu Val Thr Thr Phe
     50                  55                  60

TCT TAT GGT GTT CAA TGC TTT TCA AGA TAC CCA GAT CAT ATG AAA CGG   240
Ser Tyr Gly Val Gln Cys Phe Ser Arg Tyr Pro Asp His Met Lys Arg
 65                  70                  75                  80

CAT GAC TTT TTC AAG AGT GCC ATG CCC GAA GGT TAT GTA CAG GAA AGA   288
His Asp Phe Phe Lys Ser Ala Met Pro Glu Gly Tyr Val Gln Glu Arg
                 85                  90                  95

ACT ATA TTT TTC AAA GAT GAC GGG AAC TAC AAG ACA CGT GCT GAA GTC   336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT   384
Lys Phe Glu Gly Asp Thr Leu Val Asn Arg Ile Glu Leu Lys Gly Ile
        115                 120                 125
```

FIG. 1A

```
GAT TTT AAA GAA GAT GGA AAC ATT CTT GGA CAC AAA TTG GAA TAC AAC     432
Asp Phe Lys Glu Asp Gly Asn Ile Leu Gly His Lys Leu Glu Tyr Asn
    130                 135                     140

TAT AAC TCA CAC AAT GTA TAC ATC ATG GCA GAC AAA CAA AAG AAT GGA     480
Tyr Asn Ser His Asn Val Tyr Ile Met Ala Asp Lys Gln Lys Asn Gly
145                 150                     155                 160

ATC AAA GTT AAC TTC AAA ATT AGA CAC AAC ATT GAA GAT GGA AGC GTT     528
Ile Lys Val Asn Phe Lys Ile Arg His Asn Ile Glu Asp Gly Ser Val
                165                     170                     175

CAA CTA GCA GAC CAT TAT CAA CAA AAT ACT CCA ATT GGC GAT GGC CCT     576
Gln Leu Ala Asp His Tyr Gln Gln Asn Thr Pro Ile Gly Asp Gly Pro
            180                     185                     190

GTC CTT TTA CCA GAC AAC CAT TAC CTG TCC ACA CAA TCT GCC CTT TCG     526
Val Leu Leu Pro Asp Asn His Tyr Leu Ser Thr Gln Ser Ala Leu Ser
        195                     200                     205

AAA GAT CCC AAC GAA AAG AGA GAC CAC ATG GTC CTT CTT GAG TTT GTA     672
Lys Asp Pro Asn Glu Lys Arg Asp His Met Val Leu Leu Glu Phe Val
    210                     215                     220

ACA GCT GCT GGG ATT ACA CAT GGC ATG GAT GAA CTA TAC AAA TA          717
Thr Ala Ala Gly Ile Thr His Gly Met Asp Glu Leu Tyr Lys
225                 230                     235
```

FIG. 1B

PCR to add randomized linker
Fluorescent protein moiety
Hind III
EcoR1
Randomized linker
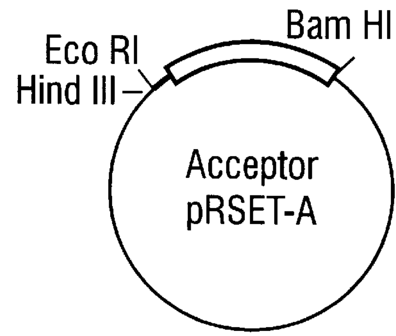
Subcloning into expression cassette containing acceptor fluorescent protein
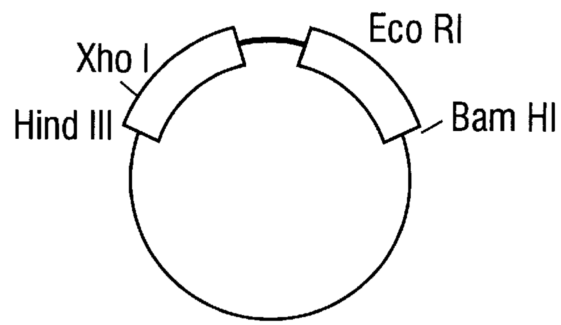
Transfection and Screening in cells to identify sequences that are cleaved when co-expressed with the target enzyme
*FIG. 10*

TANDEM FLUORESCENT PROTEIN CONSTRUCTS

This application is a continuation-in-part of U.S. Ser. No. 08/594,575, filed Jan. 31, 1996.

BACKGROUND OF THE INVENTION

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that effect the activity of proteases are natural subjects of combinatorial chemistry. Screening compounds produced by combinatorial chemistry requires convenient enzymatic assays.

The most convenient existing assays for proteases are based on fluorescence resonance energy transfer from a donor fluorophore to a quencher placed at opposite ends of a short peptide chain containing the potential cleavage site. Knight C G, "Fluorimetric assays of proteolytic enzymes," *Methods in Enzymol.* (1995) 248:18–34. Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis. However, solid phase synthesis poses certain problems of effort and expense.

It is useful to perform enzymatic assays in vivo, in order to more closely mimic conditions in which intracellular proteases act. Conventional artificial substrates prepared by solid-phase synthesis would require microinjection into individual cells, which is impractical as a high-throughput screen. Also, short unfolded peptides are generally rapidly degraded by nonspecific mechanisms inside cells.

The Edans fluorophore is the current mainstay of existing fluorometric assays. Fluorophores with greater extinction coefficients and quantum yields are desirable. The Edans fluorophore often is coupled with a non-fluorescent quencher such as Dabcyl. However, assays performed with such agents rely on the absolute measurement of fluorescence from the donor. This amount is contaminated by other factors including turbidity or background absorbances of the sample, fluctuations in the excitation intensity, and variations in the absolute amount of substrate.

SUMMARY OF THE INVENTION

This invention provides tandem fluorescent protein constructs and methods for using them in enzymatic assays both in vitro and in vivo. Tandem fluorescent protein constructs comprise a donor fluorescent protein moiety, an acceptor fluorescent protein moiety and a linker moiety that couples the donor and acceptor moieties, wherein the donor and acceptor moieties exhibit fluorescence resonance energy transfer when the donor moiety is excited. The fluorescent protein moieties can be Aequorea-related fluorescent protein moieties, such as green fluorescent protein and blue fluorescent protein. In one aspect, the linker moiety comprises a cleavage recognition site for an enzyme, and is, preferably, a peptide of between 5 and 50 amino acids. In one embodiment, the construct is a fusion protein in which the donor moiety, the peptide moiety and the acceptor moiety are part of a single polypeptide.

This invention also provides recombinant nucleic acids coding for expression of tandem fluorescent protein constructs in which a donor fluorescent protein moiety, an acceptor fluorescent protein moiety and a peptide linker moiety are encoded in a single polypeptide. The invention also provides expression vectors comprising expression control sequences operatively linked to a recombinant nucleic acid coding for the expression of a tandem fluorescent protein construct, as well as host cells transfected with those expression vectors.

The tandem constructs of this invention are useful in assays for determining whether a sample contains an enzyme. The methods involve contacting the sample with a tandem fluorescent protein construct. The donor moiety is excited. Then the degree of fluorescence resonance energy transfer in the sample is determined. A degree of fluorescence resonance energy transfer that is lower than an expected amount indicates the presence of an enzyme. The degree of fluorescence resonance energy transfer in the sample can be determined as a function of the amount of fluorescence from the donor moiety, the amount of fluorescence from the acceptor donor moiety, the ratio of the amount of fluorescence from the donor moiety to the amount of fluorescence from the acceptor moiety or the excitation state lifetime of the donor moiety.

The assay also is useful for determining the amount of enzyme in a sample by determining the degree of fluorescence resonance energy transfer at a first and second time after contact between the enzyme and the tandem construct, and determining the difference in the degree of fluorescence resonance energy transfer. The difference in the degree of fluorescence resonance energy transfer reflects the amount of enzyme in the sample.

The invention also provides methods for determining the amount of activity of an enzyme in a cell. The methods involve providing a cell that expresses a tandem fluorescent protein construct, for example by transfecting the cell with an appropriate expression vector. The cell is exposed to light in order to excite the donor moiety. Then the degree of fluorescence resonance energy transfer in the cell is determined. The degree of fluorescence resonance energy transfer reflects to the amount of enzyme activity in the cell.

Similarly, the invention provides methods of determining the amount of activity of an enzyme in a sample from an organism. The methods involve providing a sample from an organism having a cell that expresses a tandem fluorescent protein construct. The donor moiety in the sample is excited. Then the degree of fluorescence resonance energy transfer in the sample is determined. The degree of fluorescence resonance energy transfer reflects the amount of enzyme activity in the cell.

The assay methods also can be used to determine whether a compound alters the activity of an enzyme, i.e., screening assays. The methods involve contacting a sample containing an amount of the enzyme with the compound and with a tandem fluorescent protein construct; exciting the donor moiety; determining the amount of enzyme activity in the sample as a function of the degree of fluorescence resonance energy transfer in the sample; and comparing the amount of activity in the sample with a standard activity for the same amount of the enzyme. A difference between the amount of enzyme activity in the sample and the standard activity indicates that the compound alters the activity of the enzyme.

Similar methods, are useful for determining whether a compound alters the activity of an enzyme in a cell. The methods involve providing first and second cells that express a tandem fluorescent protein construct; contacting the first cell with an amount of the compound; contacting the second cell with a different amount of the compound; exciting the donor moiety in the first and second cell; determining the degree of fluorescence resonance energy transfer in the first and second cells; and comparing the degree of fluorescence resonance energy transfer in the first and second cells. A difference in the degree of fluorescence resonance energy transfer indicates that the compound alters the activity of the enzyme.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent protein moieties each linked by a randomized linker moiety can be generated using recombinant engineering techniques or synthetic chemistry techniques. Screening the members of the library can be accomplished by measuring a signal related to cleavage, such as fluorescence energy transfer, after contacting the cleavage enzyme with each of the library members of the tandem fluorescent protein construct. A degree of fluorescence resonance energy transfer that is lower than an expected amount indicates the presence of a linker sequence that can be cleaved by the enzyme. The degree of fluorescence resonance energy transfer in the sample can be determined as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

Libraries of fluorescent proteins can be expressed in cells and used to characterize the recognition motif of proteases expressed within cells, where the enzyme is in its native context. This method provides the additional advantage of assessing the specificity of any given linker sequence to cleavage by other enzymes other than the target enzyme. The methods consist of the generation of a library of recombinant host cells, each of which expresses a tandem fluorescent protein construct linked through a randomized candidate linker substrate. Each cell is expanded into a clonal population that is genetically homogeneous and the degree of energy transfer is measured from each clonal population. Optionally, FRETS can be measured before and at least one specified time after a known change in intracellular protease activity. A change in the degree of fluorescence resonance energy transfer demonstrates that the cell contains a tandem construct and linker sequence that can be cleaved by the enzyme activity in the cell. Such methods are particular suited to Fluorescent Activated Cell Sorter (FACS) clonal selection.

BRIEF DESCRIPTION OF THE DRAWINGS

FIG. 1 depicts the nucleotide sequence (SEQ ID NO:1) and deduced amino acid sequence (SEQ ID NO:2) of a wild-type Aequorea green fluorescent protein.

FIG. 10 depicts a method of generating fluorescent tandem constructs separated by a randomized linker region for use in identifying cleavage specificities or orphan proteases.

DETAILED DESCRIPTION OF THE INVENTION

DEFINITIONS

Figure 2:
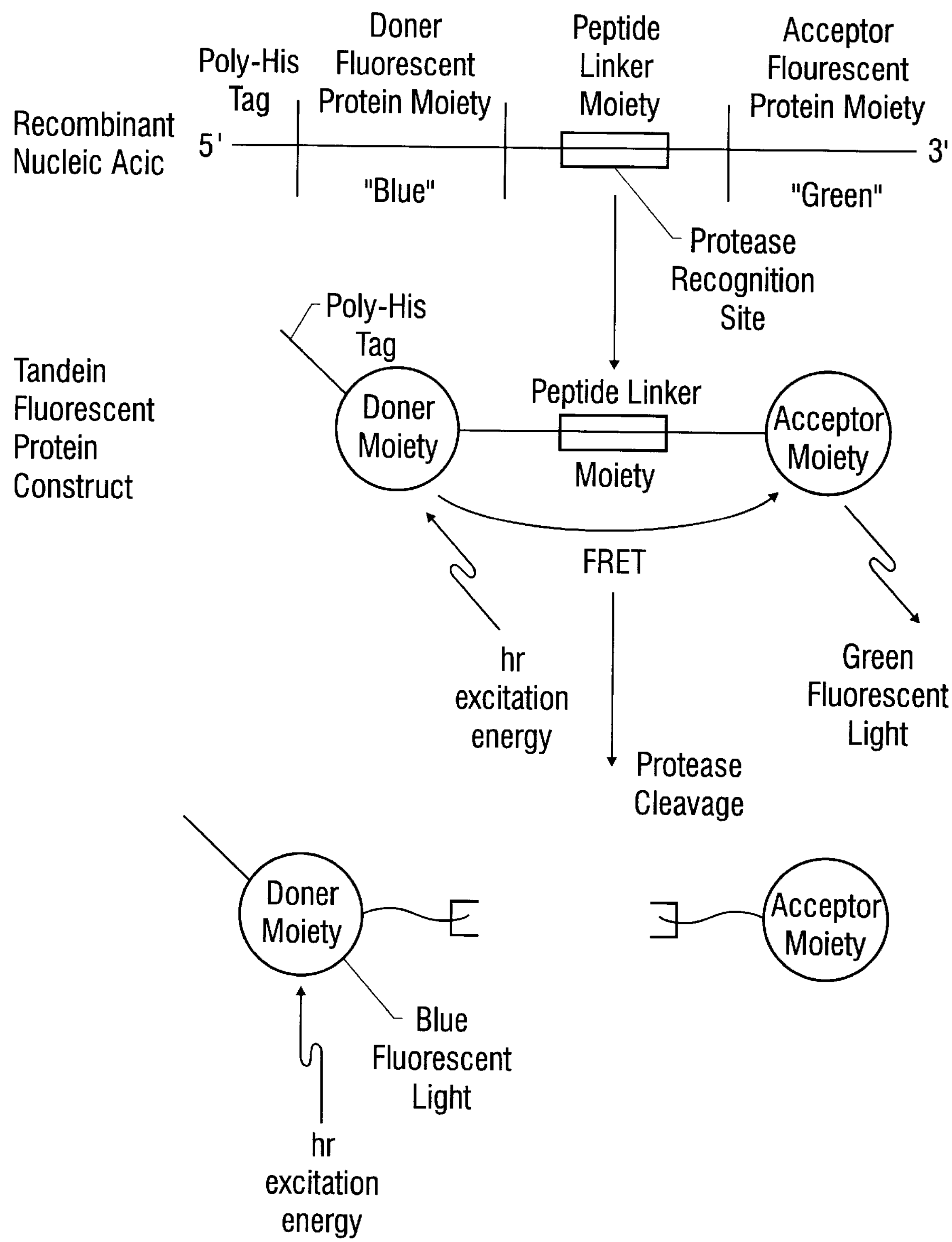
FIG. 2 depicts a tandem construct of the invention involved in FRET.

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients. As employed throughout the disclosure, the following terms, unless otherwise indicated, shall be understood to have the following meanings:

"Moiety" refers to the radical of a molecule that is attached to another moiety. Thus, a "fluorescent protein moiety" is the radical of a fluorescent protein coupled to the linker moiety. By the same token, the term "linker moiety" refers to the radical of a molecular linker that is coupled to both the donor and acceptor protein moieties.

"Fluorescent protein" refers to any protein capable of fluorescence when excited with appropriate electromagnetic radiation. This includes fluorescent proteins whose amino acid sequences are either natural or engineered.

"Peptide" refers to a polymer in which the monomers are amino acids and are joined together through amide bonds, alternatively referred to as a polypeptide. When the amino acids are a-amino acids, either the L-optical isomer or the D-optical isomer may be used. Additionally, unnatural amino acids, for example, b-alanine, phenylglycine and homoarginine are also meant to be included. Commonly encountered amino acids which are not gene-encoded may also be used in the present invention. All of the amino acids used in the present invention may be either the D- or L-isomer. The L-isomers are preferred. In addition, other peptidomimetics are also useful in the linker moieties of the present invention. For a general review see Spatola, A. F., in *Chemistry and Biochemistry of Amino Acids, Peptides and Proteins,* B. Weinstein, eds., Marcel Dekker, New York, p. 267 (1983).

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length, either ribonucleotides or deoxynucleotides or a modified form of either type of nucleotide. The term includes single and double stranded forms of DNA.

"Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "modulator" refers to a chemical compound (naturally occurring or non-naturally occurring), such as a biological macromolecule (e.g. nucleic acid, protein, non-peptide, or organic molecule), or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partial known. Such modulators can be screened using the methods described herein.

The term "test compound" refers to a compound to be tested by one or more screening method(s) of the invention as a putative modulator. Usually, various predetermined concentrations are used for screening such as 0.01 uM, 0.1 uM, 1.0 uM, and 10.0 uM. Test compound controls can include the measurement of a signal in the absence of the test compound or comparison to a compound known to modulate the target.

INTRODUCTION

It has been discovered that fluorescent proteins having the proper emission and excitation spectra that are brought into physically close proximity with one another can exhibit fluorescence resonance energy transfer ("FRET"). This invention takes advantage of that discovery to provide tandem fluorescent protein constructs in which two fluorescent protein moieties capable of exhibiting FRET are coupled through a linker to form a tandem construct. The protein moieties are chosen such that the excitation spectrum of one of the moieties (the acceptor moiety) overlaps with the emission spectrum of the excited protein moiety (the donor moiety). The donor moiety is excited by light of appropriate intensity within the donor's excitation spectrum. The donor then emits the absorbed energy as fluorescent light. The fluorescent energy it produces is quenched by the acceptor fluorescent protein moiety. FRET can be manifested as a reduction in the intensity of the fluorescent signal from the donor, reduction in the lifetime of its excited state, and re-emission of fluorescent light at the longer wavelengths (lower energies) characteristic of the acceptor. When the linker that connects the donor and acceptor moieties is cleaved, the fluorescent proteins physically separate, and FRET is diminished or eliminated. This has also been described in U.S. patent application Ser. No. 08/594,575, filed Jan. 31, 1996, which is herein incorporated by reference.

One can take advantage of the FRET exhibited by the tandem fluorescent protein constructs of the invention in performing enzymatic assays. An embodiment of this process is depicted in FIG. 2. A recombinant nucleic acid encodes a single polypeptide including a poly-histidinyl tag, a blue fluorescent protein donor moiety, a peptide linker moiety comprising a protease recognition site and a green fluorescent protein acceptor moiety. The nucleic acid can be expressed into a tandem fluorescent protein construct of the invention. In this example, a tandem construct contains a blue fluorescent protein (such as P4-3, TABLE I) as the donor moiety and a green fluorescent protein (such as S65C, TABLE I) as the acceptor moiety.

The construct is exposed to light at, for example, 368 nm, a wavelength that is near the excitation maximum of P4-3. This wavelength excites S65C only minimally. Upon excitation, some portion of the energy absorbed by the blue fluorescent protein moiety is transferred to the acceptor moiety through FRET. As a result of this quenching, the blue fluorescent light emitted by the blue fluorescent protein is less bright than would be expected if the blue fluorescent protein existed in isolation. The acceptor moiety (S65C) may re-emit the energy at longer wavelength, in this case, green fluorescent light.

After cleavage of the linker moiety by an enzyme, the blue and green fluorescent proteins physically separate and FRET is lost. Over time, as increasing amounts of the tandem construct are cleaved, the intensity of visible blue fluorescent light emitted by the blue fluorescent protein increases, while the intensity of visible green light emitted by the green fluorescent protein as a result of FRET, decreases.

The tandem fluorescent protein constructs of this invention are useful as substrates to study agents or conditions that cleave the linker. In particular, this invention contemplates tandem constructs in which the linker is a peptide moiety containing an amino acid sequence that is a cleavage site for a protease of interest. The amount of the protease in a sample is determined by contacting the sample with a tandem fluorescent protein construct and measuring changes in fluorescence of the donor moiety, the acceptor moiety or the relative fluorescence of both. In one embodiment, the tandem construct is a recombinant fusion protein produced by expression of a nucleic acid that encodes a single polypeptide containing the donor moiety, the peptide linker moiety and the acceptor moiety. Fusion proteins can be used for, among other things, monitoring the activity of a protease inside the cell that expresses the recombinant tandem construct. The distance between fluorescent proteins in the construct can be regulated based on the length of the linking moiety. Therefore, tandem constructs of this invention whose linker moieties do not include cleavage sites also are useful as agents for studying FRET between fluorescent proteins.

Advantages of tandem fluorescent protein constructs include the greater extinction coefficient and quantum yield of many of these proteins compared with those of the Edans fluorophore. Also, the acceptor in a tandem construct is, itself, a fluorophore rather than a non-fluorescent quencher like Dabcyl. Thus, the enzyme's substrate (i.e., the tandem construct) and products (i.e., the moieties after cleavage) are both fluorescent but with different fluorescent characteristics.

In particular, the substrate and cleavage products exhibit different ratios between the amount of light emitted by the donor and acceptor moieties. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, the Aequorea-related fluorescent protein moieties tend to be protease resistant. Therefore, they are likely to survive as fluorescent moieties even after the linker moiety is cleaved.

II. TANDEM FLUORESCENT PROTEIN CONSTRUCTS

The tandem fluorescent protein constructs of the invention usually comprise three elements: a donor fluorescent protein moiety, an acceptor fluorescent protein moiety and a linker moiety that couples the donor and acceptor moieties. The donor fluorescent protein moiety is capable of absorbing a photon and transferring energy to another fluorescent moiety. The acceptor fluorescent protein moiety is capable of absorbing energy and emitting a photon. The linker moiety connects the donor fluorescent protein moiety to the acceptor fluorescent protein moiety. In many instances the linker moiety will covalently connect the donor fluorescent protein moiety and the acceptor fluorescent protein moiety. It is desirable, as described in greater detail herein, to select a donor fluorescent protein moiety with an emission spectrum that overlaps with the excitation spectrum of an acceptor fluorescent protein moiety. In some embodiments of the invention the overlap in emission and excitation spectra will facilitate FRET, Such an overlap is not necessary, however, if intrinsic fluorescence is measured instead of FRET. Any fluorescent protein may be used in the invention, including proteins that have fluoresce due intramolecular rearrangements or the addition of cofactors that promote fluorescence.

For example, green fluorescent proteins ("GFPs") of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, the sea pansy, *Renilla reniformis*, and *Phialidium gregarium*. W. W. Ward et al., *Photochem. Photobiol.,* 35:803–808 (1982); L. D. Levine et al., *Comp. Biochem. Physiol.,* 72B:77–85 (1982).

A variety of Aequorea-related GFPs having useful excitation and emission spectra have been engineered by modifying the amino acid sequence of a naturally occurring GFP from *Aequorea victoria*. (D. C. Prasher et al., *Gene,* 111:229–233 (1992); R. Heim et al., *Proc. Natl. Acad. Sci., USA,* 91:12501–04 (1994); U.S. patent application Ser. No. 08/337,915, filed Nov. 10, 1994; International application PCT/US95/14692, filed Nov. 10, 1995; U.S. patent application Ser. No. 08/706,408, filed Aug. 30, 1996.The green fluorescent protein (GFP) of the jellyfish *Aequorea victoria* is a remarkable protein with strong visible absorbance and fluorescence from a p-hdroxybenzlideneimidazolone chromophore, which is generated by cyclization and oxidation of the protein's own Ser-Tyr-Gly sequence at positions 65 to 67. A cDNA sequence for one isotype of GFP has been reported [Prasher, D. C. et al., Gene 111, 229–233 (1992)]. The finding that the expressed protein becomes fluorescent in cells from a wide variety of organisms [Chalfie, M. et al., Science 263, 802–805 (1994)] makes GFP a powerful new tool in molecular and cell biology and indicates that the oxidative cyclization must be either spontaneous or dependent only on ubiquitous enzymes and reactants. As used herein, a fluorescent protein is an Aequorea-related fluorescent protein if any contiguous sequence of 150 amino acids of the fluorescent protein has at least 85% sequence identity with an amino acid sequence, either contiguous or non-contiguous, from the wild type Aequorea green fluorescent protein of SEQ ID NO:2. More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein of SEQ ID NO:2. Similarly, the fluorescent protein may be related to Renilla or Phialidium wild-type fluorescent proteins using the same standards.

Aequorea-related fluorescent proteins include, for example, wild-type (native) *Aequorea victoria* GFP, whose nucleotide (SEQ ID NO:1) and deduced amino acid (SEQ ID NO:2) sequences are presented in FIG. 1; and those Aequorea-related engineered versions described in TABLE I. Several of these, i.e., P4, P4-3, W7 and W2 fluoresce at a distinctly shorter wavelength than wild type.

TABLE I

| Clone | Mutation(s) | Excitation max (nm) | Emission max (nm) | Extinct. Coefficient ($M^{-1}cm^{-1}$) | Quantum yield |
|---|---|---|---|---|---|
| Wild type | None | 393 (475) | 508 | 21,000 (7,150) | 0.77 |
| P4 | Y66H | 383 | 447 | 13,500 | 0.21 |
| P4-3 | Y66H<br>Y145F | 381 | 445 | 14,000 | 0.38 |
| W7 | Y66W<br>N146L<br>M153T<br>V163A<br>N212K | 433 (453) | 475 (501) | 18,000<br>(17,100) | 0.67 |
| W2 | Y66W<br>I123V<br>Y145H<br>H148R<br>M153T<br>V163A<br>N212K | 432 (453) | 480 | 10,000 (9,600) | 0.72 |
| S65T | S65T | 489 | 511 | 39,200 | 0.68 |
| P4-I | S65T<br>M153A<br>K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| 10c | S65G<br>V68L<br>V72A<br>T203Y | 513 | 527 | | |
| W1B | F64L<br>S65T<br>Y66W<br>N146I<br>M153T<br>V163A<br>N212K | 432 (453) | 476 (503) | | |
| Emerald | S65T<br>S72A<br>N149K<br>M153T<br>I167T | 487 | 508 | | |
| Sapphire | S72A<br>Y145F<br>T203I | 395 | 511 | | |

This invention contemplates the use of other fluorescent proteins in tandem constructs. The cloning and expression of yellow fluorescent protein from *Vibrio fischeri* strain Y-1 has been described by T. O. Baldwin et al., *Biochemistry.* (1990) 29:5509–15. This protein requires flavins as fluorescent co-factors. The cloning of Peridinin-chlorophyll a binding protein from the dinoflagellate Symbiodinium sp. was described by B. J. Morris et al., *Plant Molecular Biology,* (1994) 24:673:77. One useful aspect of this protein is that it fluoresces in red. The cloning of phycobiliproteins from marine cyanobacteria such as Synechococcus, e.g., phycoerythrin and phycocyanin, is described in S. M. Wilbanks et al., *J. Biol. Chem.* (1993) 268:1226–35. These proteins require phycobilins as fluorescent co-factors, whose insertion into the proteins involves auxiliary enzymes. The proteins fluoresce at yellow to red wavelengths.

For FRET, the donor fluorescent protein moiety and the acceptor fluorescent protein moiety are selected so that the donor and acceptor moieties exhibit fluorescence resonance energy transfer when the donor moiety is excited. One factor to be considered in choosing the fluorescent protein moiety pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods described herein and known in the art, particularly, using the conditions set forth in the Examples.

The efficiency of FRET is dependent on the separation distance and the orientation of the donor and acceptor moieties, as described by the Forster equation, the fluorescent quantum yield of the donor moiety and the energetic overlap with the acceptor moiety. Forster derived the relationship:

$$E=(F^0-F)/F^0=R_0^6/(R^6+R_0^6)$$

where E is the efficiency of FRET, F and $F^0$ are the fluorescence intensities of the donor in the presence and absence of the acceptor, respectively, and R is the distance between the donor and the acceptor. $R_0$, the distance at which the energy transfer efficiency is 50%, is given (in Å) by $$R_0=9.79\times10^3(K^2QJn^{-4})^{1/6}$$

where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap, $$J=\int_0^\infty \epsilon_\lambda F_\lambda \lambda^4 d\lambda / \int_0^\infty F_\lambda d\lambda$$

where $\epsilon_\lambda$ is the molar absorptivity of the acceptor in $M^{-1}$ $cm^{-1}$ and $F_\lambda$ is the donor fluorescence at wavelength 1 measured in cm. Forster, T. (1948) *Ann. Physik* 2:55–75. Tables of spectral overlap integrals are readily available to those working in the field (for example, Berlman, I. B. *Energy transfer parameters of aromatic compounds,* Academic Press, New York and London (1973)).

The characteristic distance $R_0$ at which FRET is 50% efficient depends on the quantum yield of the donor i.e., the shorter-wavelength fluorophore, the extinction coefficient of the acceptor, i.e., the longer-wavelength fluorophore, and the overlap between the donor's emission spectrum and the acceptor's excitation spectrum. Calculated values of $R_0$ for P4-3 to S65T and S65C are both 4.03 nm because the slightly higher extinction coefficient of S65T compensates for its slightly longer emission wavelength. R. Heim et al., "Improved green fluorescence," *Nature* (1995) 373:663–664.

The efficiency of FRET between the two fluorescent proteins can also be adjusted by changing ability of the two fluorescent proteins to dimerize or closely associate. If the two fluorescent proteins are known or determined to closely associate, an increase or decrease in dimerization can be promoted by adjusting the length of the linker moiety between the two fluorescent proteins. Such dimerization can change $\Lambda^2$, R, J, and Q and dimerization changes directly affect the fluorescence spectra compared to undimerized protein. Consequently, for FRET aspects of the invention, the change in intrinsic fluorescence can be used to adjust the amount of FRET between the donor and the acceptor, as well as dimerization induced changes in FRET distances. Such dimerization induced changes in FRET distance can be optimized for maximal changes in FRET upon cleavage of a linker moiety by empirically determining the length of the linker moiety that produces the best FRET. Usually, such linkers will be comparable to a length of 14 to 30 amino acids.

The ability of two fluorescent proteins to dimerize could be increased by selecting amino acid positions that interact in the dimer and making changes of the amino acids at such positions that increase the hydrophobic or ionic interactions, or decrease the steric repulsions. Conversely, ability of two fluorescent proteins to dimerize could be decreased by selecting amino acid positions that interact in the dimer and making changes in the amino acids at such positions that decrease the hydrophobic or ionic interaction, or increase the steric repulsions. Thus, intramolecular interactions responsible for the association of fluorescent protein moieties in a tandem fluorescent protein or intermolecular interactions between two fluorescent proteins in free solution can be enhanced or attenuated.

For example, Aequorea derived fluorescent proteins and related proteins, especially at high concentrations of free protein, exist as dimers. The dimerization domain can be identified in the wild type protein using the crystal structure. Yang, F., et al The Molecular structure of Green Fluorescent Protein. Nature. Biotech. (1996) 14 1246–1251. In the case of wildtype GFP, the hydrophobic amino acids, Ala 206, Leu 221, and Phe 223 interact during dimerization. The tendency of a tandem GFP (or two GFPs in free solution)to non-covalently associate at these positions could be increased by increasing the hydrophobicity of amino acids at positions 206 or 221, thereby increasing the strength of hydrophobic interactions between the two fluorescent proteins.

For example, replacement of Ala 206, or Leu 221 by any of the amino acids, Val, Ile or Phe would increase their hydrophobicity, and potentially strengthen the hydrophobic interaction between two GFPs. Alternatively, the amino acids could be changed to positively charged amino acids in one fluorescent protein (for example lys or Arg) and to negatively charged amino acids in the second fluorescent protein of the construct (for example Glu or Asp) thereby creating additional electrostatic interactions between two GFPs. Similarly the amino acids Tyr 39, Glu 142, Asn 144, Asn 146, Ser 147, Asn 149, Tyr 151, Arg 168, Asn 170, Glu 172, Tyr 200, Ser 202, Gln 204 and Ser 208 could be changed according to the methods described herein to enhance intramolecular interactions between tandem fluorescent proteins or intermolecular interactions between to GFPs in free solution.

The length of the linker moiety is chosen to optimize both FRET and the kinetics and specificity of enzymatic cleavage. The average distance between the donor and acceptor moieties should be between about 1 nm and about 10 nm, preferably between about 1 nm and about 6 nm, and more preferably between about 1 nm and about 4 nm. If the linker is too short, the protein moieties may sterically interfere with each other's folding or with the ability of the cleavage enzyme to attack the linker. In embodiments of the invention where dimerization is desired the linker length will typically be a length comparable the length of at least 12 amino acids, preferably at least 18 amino acids and more preferably at least 24 amino acids. Only in rare instances will the linker length be longer than the length of about 40 to 50 amino acids. However, embodiments of the invention comprise linker moieties having 150 to 200 amino acids.

The effect of linker length on the ability of tandemly linked fluorescent proteins to become fluorescent was determined for a modified GFP tandem protein, as shown in TABLE II. The modified GFP tandem protein was expressed in bacteria and grown at 37(C.

TABLE II

| Linker Length in amino acids | Fluorescence of 1st Fluorescent protein (Sapphire) | Fluorescence of 2nd Fluorescent protein (10C) |
|---|---|---|
| 12 | $6.8 \times 10^4$ | $6.2 \times 10^4$ |
| 14 | $8.9 \times 10^4$ | $8.4 \times 10^4$ |
| 16 | $1.1 \times 10^5$ | $1.0 \times 10^5$ |
| 18 | $1.3 \times 10^5$ | $1.2 \times 10^5$ |
| 20 | $1.5 \times 10^5$ | $1.4 \times 10^5$ |
| 22 | $2.9 \times 10^5$ | $1.6 \times 10^5$ |
| 24 | $1.1 \times 10^6$ | $7.8 \times 10^4$ |
| 25 | $2.0 \times 10^6$ | $1.2 \times 10^6$ |

Tandem fluorescent proteins of the invention comprising the general form Sapphire—linker—10C (10C is also known as Topaz) were expressed in the bacterial cells JM109 (DE3). The linker moiety was constructed with variable numbers of amino acids to evaluate the influence of linker size on fluorescence development. The linker sequences of TABLE II are described as SEQ ID NO.: 26 to 31, respectively. The composition of the 25 amino acid linker is identical to that used in the tandem fluorescent protein constructs in the Examples. After overnight growth at 37(C. the bacterial colonies were examined to determine their relative fluorescence by resuspension in PBS after normalization for the number of bacteria present by measuring the optical density at 600 nm.

When the intramolecular dimerization of a tandem fluorescent protein construct is preferred, the three dimensional structure and flexability of the linker should permit the fluorescent protein moieties to associate. When the linker moiety contains a cleavage site, the length of the linker can be between about 5 and about 50 amino acids and more preferably between about 12 and 30 amino acids. Longer linkers may create too many sites which are vulnerable to attack by enzymes other than the one being assayed.

To optimize the efficiency and detectability of FRET within the tandem fluorescent protein construct, several factors need to be balanced. The emission spectrum of the donor moiety should overlap as much as possible with the excitation spectrum of the acceptor moiety to maximize the overlap integral J. Also, the quantum yield of the donor moiety and the extinction coefficient of the acceptor should likewise be as high as possible to maximize $R_0$. However, the excitation spectra of the donor and acceptor moieties should overlap as little as possible so that a wavelength region can be found at which the donor can be excited efficiently without directly exciting the acceptor. Fluorescence arising from direct excitation of the acceptor is difficult to distinguish from fluorescence arising from FRET. Similarly, the emission spectra of the donor and acceptor moieties should overlap as little as possible so that the two emissions can be clearly distinguished. High fluorescence quantum yield of the acceptor moiety is desirable if the emission from the acceptor is to be measured either as the sole readout or as part of an emission ratio. In a preferred embodiment, the donor moiety is excited by ultraviolet (<400 nm) and emits blue light (<500 nm), whereas the acceptor is efficiently excited by blue but not by ultraviolet light and emits green light (>500 nm), for example, P4-3 and S65C.

In the tandem constructs of the invention, the donor and acceptor moieties are connected through a linker moiety. The linker moiety is, preferably, a peptide moiety, but can be another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the fluorescent protein moieties that is measurable as a change in FRET.

When the cleavage agent of interest is a protease, the linker can comprise a peptide containing a cleavage recognition sequence for the protease. A cleavage recognition sequence for a protease is a specific amino acid sequence recognized by the protease during proteolytic cleavage. In particular, the linker can contain any of the amino acid sequences in TABLE III. The sites are recognized by the enzymes as indicated and the site of cleavage is marked by a hyphen. Other protease cleavage sites also are known in the art and can be included in the linker moiety.

TABLE III

| Protease | Sequence |
|---|---|
| HIV-1 protease | SQNY-PIVQ (SEQ ID NO: 3)<br>KARVL-AEAMS (SEQ ID NO: 4) |
| Prohormone convertase | PSPREGKR-SY (SEQ ID NO: 5) |
| Interleukin-1b-converting enzyme | YVAD-G (SEQ ID NO: 6) |
| Adenovirus endopeptidase | MFGG-AKKR (SEQ ID NO: 7) |
| Cytomegalovirus assemblin | GVVNA-SSRLA (SEQ ID NO: 8) |
| Leishmanolysin | LIAY-LKKAT (SEQ ID NO: 9) |
| b-Secretase for amyloid precursor protein | VKM-DAEF (SEQ ID NO: 10) |
| Thrombin | FLAEGGGVR-GPRVVERH (SEQ ID NO: 11) |
| Renin and angiotensin-converting enzyme | DRVYIHPF-HL-VIH (SEQ ID NO: 12) |
| Cathepsin D | KPALF-FRL (SEQ ID NO: 13) |
| Kininogenases including kallikrein | QPLGQTSLMK-RPPGFSPFR- SVQVMKT QEGS (SEQ ID NO: 14) |

See, e.g., Matayoshi et al. (1990) Science 247:954, Dunn et al. (1994) Meth. Enzymol. 241:254, Seidah & Chretien (1994) Meth. Enzymol. 244:175, Thornberry (1994) Meth. Enzymol. 244:615, Weber & Tihanyi (1994) Meth. Enzymol. 244:595, Smith et al. (1994) Meth. Enzymol. 244:412, Bouvier et al. (1995) Meth. Enzymol. 248:614, Hardy et al. (1994) in Amyloid Protein Precursor in Development, Aging, and Alzheimer's Disease, ed. C. L. Masters et al. pp. 190–198.

In the case of a known protease with cleavage activity of unknown or partially defined specificity, a library of randomized linker sequences can be used in place of a predetermined linker sequence in the tandem fluorescent protein construct in order to determine the sequences cleaved by a protease. The method can be used with a recombinant protease constructed with a novel cleavage specificity. This method can also be used to determine the specificity of cleavage of an orphan protein that reveals sequence homology to a known protease structure or group of proteases.

In one embodiment, a genetically engineered library of tandem fluorescent protein constructs having randomized linkers can be used to define the function of an orphan protease. Optionally, the orphan protease, especially to if is thought to be expressed relatively inactive precursor, can be coexpressed with the tandem fluorescent protein construct. The protease may also be coexpressed with the tandem construct and under the control of an inducable promoter.

As used herein, a "library" refers to a collection containing at least 5 different members, preferably at least 100 different members and more preferably at least 200 different members. Each member of a tandem fluorescent substrate library comprises 2 tandemly linked fluorescent protein moieties separated by a peptide linker moiety of variable amino acid composition. The amino acid sequences for the peptide linker moiety may be completely random or biased towards a particular sequence based on the homology between other proteases and the protease being tested. The library can be chemically synthesized, which is particularly desirable if d-amino acids are to be included. In most instances, however, the library will be expressed in bacteria or a mammalian cell.

For example, the library can contain linkers with a diverse collection of amino acids in which most or all of the amino acid positions are randomized. Alternatively, the library can contain variable peptide moieties in which only a few, e.g., one to ten, amino acid positions are varied, but in which the probability of substitution is very high.

Preferably, libraries of tandem fluorescent protein candidate substrates are created by expressing protein from libraries of recombinant nucleic acid molecules having expression control sequences operatively linked to nucleic acid sequences that code for the expression of different fluorescent protein candidate substrates. Methods of making nucleic acid molecules encoding a diverse collection of peptides are described in, for example, U.S. Pat. No. 5,432,018 (Dower et al.), U.S. Pat. No. 5,223,409 (Ladner et al.) and International patent publication WO 92/06176 (Huse et al.).

For expression of tandem fluorescent protein candidate substrates, recombinant nucleic acid molecules are used to transfect cells, such that a cell contains a member of the library. This produces, in turn, a library of host cells capable of expressing a library of different fluorescent protein candidate substrates. The library of host cells is useful in the screening methods of this invention.

In one method of creating such a library, a diverse collection of oligonucleotides having random codon sequences are combined to create polynucleotides encoding peptides having a desired number of amino acids for the lnker moiety. The oligonucleotides preferably are prepared by chemical syntheses. The polynucleotides encoding peptide linker moiety of variable composition can then be ligated to the 5' or 3' end of a nucleic acid encoding one of the tandem fluorescent protein moieties, using methods known in the art. This creates a recombinant nucleic acid molecule coding for the expression of a fluorescent protein candidate substrate having a variable linker peptide moiety fused to the amino or carboxy- terminus of one of the tandem fluorescent proteins. This recombinant nucleic acid molecule is then inserted into an expression vector in which the second fluorescent has already been inserted to create a recombinant nucleic acid molecule comprising expression control sequences operatively linked to the sequences encoding the tandemly repeated fluorescent proteins separated by the linker moieties (FIG. 10).

To generate the collection of oligonucleotides which forms a series of codons encoding a random collection of amino acids that is ultimately cloned into the vector, a codon motif is used, such as $(NNK)_x$, where N may be A, C, G, or T (nominally equimolar), K is G or T (nominally equimolar), and x is the desired number of amino acids in the peptide moiety, e.g., 15 to produce a library of 15-mer peptides. The third position may also be G or C, designated "S". Thus, NNK or NNS (i) code for all the amino acids, (ii) code for only one stop codon, and (iii) reduce the range of codon bias from 6:1 to 3:1. The expression of peptides from randomly generated mixtures of oligonucleotides in appropriate recombinant vectors is discussed in Oliphant et al., *Gene* 44:177–183 (1986), incorporated herein by reference.

An exemplified codon motif $(NNK)_6$ produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias for amino acids encoded by two or threes alternative codons.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5-HO-protecting groups, and activating by the addition of 3'O-phosphoramidite (and phosphate protection with beta-cyanoethyl groups) by the method used for the activation of mononucleosides, as generally described in McBride and Caruthers, *Tetrahedron Letters* 22:245 (1983). Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis,* M. J. Gait, ed. p35–82 (1984). Thus, this procedure generates a population of oligonucleotides for cloning that is capable of encoding an equal distribution (or a controlled unequal distribution) of the possible peptide sequences.

Because protease cleavage recognition sequences generally are only a few amino acids in length, the linker moiety can include the recognition sequence within flexible spacer amino acid sequences, such as GGGGS (SEQ ID NO:15). For example, a linker moiety including a cleavage recognition sequence for Adenovirus endopeptidase could have the sequence GGGGGGSMFG GAKKRSGGGG GG (SEQ ID NO:16).

Alternatively, the linker moiety can be an organic molecular moiety that can contain a cleavage site for an enzyme that is not a protease. The molecular structure is selected so that the distance between the fluorescent moieties allows FRET (i.e., less than about 10 nm). For example, the linker moiety can contain a structure that is recognized by b-lactamase, rendering the tandem complex a substrate for this enzyme. One structure for such a linker moiety is:

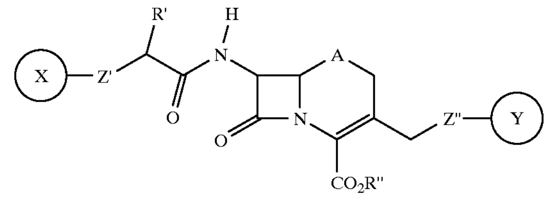

in which one of X and Y is the donor moiety and the other is the acceptor moiety. R' can be, for example, H, lower alkyl or lower alkoxy of up to 15 carbon. R" can be H, physiologically-acceptable metal and ammonium cations, alkyl, alkoxy or aromatic groups of up to 15 carbon atoms. (See, e.g., Bundgaard, H., *Design of prodrugs,* Elsevier Science publishers (1985); *Bioreversible Carriers in Drug Design,* New York:Pergamon Press (1987); Ferres, H. (1980) *Chem. Ind.* June:435–440.) Z' and Z" are parts of the linker moiety having fewer than about 20 carbon atoms. Z" includes a heteroatom, such as oxygen or, preferably, sulfur, attached to the cephalosporin side chain to act as a nucleofuge. Such linker moieties also are described in U.S. patent application Ser. No. 08/407,547, filed Mar. 20, 1995.

This invention contemplates tandem fluorescent protein constructs produced in the form of a fusion protein by recombinant DNA technology as well as constructs produced by chemically coupling fluorescent proteins to a linker. In either case, the fluorescent proteins for use as donor or acceptor moieties in a tandem construct of the invention preferably are produced recombinantly.

Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of cDNA from *A. victoria* using primers based on the DNA sequence of *A. victoria* green fluorescent protein, as presented in FIG. 1. PCR methods are described in, for example, U.S. Pat. No. 4,683,195; Mullis et al. (1987) *Cold Spring Harbor Symp. Quant. Biol.* 51:263; and Erlich, ed., *PCR Technology,* (Stockton Press, New York, 1989). Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations. See, e.g., U.S. patent application Ser. No. 08/337,915, filed Nov. 10, 1994 or International application PCT/US95/14692, filed Nov. 10, 1995.

The construction of expression vectors and the expression of genes in transfected cells involves the use of molecular cloning techniques also well known in the art. Sambrook et al., *Molecular Cloning—A Laboratory Manual,* Cold Spring Harbor Laboratory, Cold Spring Harbor, N.Y., (1989) and *Current Protocols in Molecular Biology,* F. M. Ausubel et al., eds., (Current Protocols, a joint venture between Greene Publishing Associates, Inc. and John Wiley & Sons, Inc., (most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Recombinant fluorescent protein can be produced by expression of nucleic acid encoding the protein in *E. coli*. The fluorophore of Aequorea-related fluorescent proteins results from cyclization and oxidation of residues 65–67. Aequorea-related fluorescent proteins are best expressed by cells cultured between about 20° C. and 30° C. After synthesis, these enzymes are stable at higher temperatures (e.g., 37° C.) and can be used in assays at those temperatures.

The construct can also contain a tag to simplify isolation of the tandem construct. For example, a polyhistidine tag of, e.g., six histidine residues, can be incorporated at the amino terminal end of the fluorescent protein. The polyhistidine tag allows convenient isolation of the protein in a single step by nickel-chelate chromatography.

A. Recombinant Nucleic Acids Encoding Tandem Construct Fusion Proteins

In a preferred embodiment, the tandem construct is a fusion protein produced by recombinant DNA technology in which a single polypeptide includes a donor moiety, a peptide linker moiety and an acceptor moiety. The donor moiety can be positioned at the amino-terminus relative to the acceptor moiety in the polypeptide. Such a fusion protein has the generalized structure: (amino terminus) donor fluorescent protein moiety—peptide linker moiety—acceptor fluorescent protein moiety (carboxy terminus). Alternatively, the donor moiety can be positioned at the carboxy-terminus relative to the acceptor moiety within the fusion protein. Such a fusion protein has the generalized structure: (amino terminus) acceptor fluorescent protein moiety—peptide linker moiety—donor fluorescent protein moiety (carboxy terminus). The invention also envisions fusion proteins that contain extra amino acid sequences at the amino and/or carboxy termini, for example, polyhistidine tags.

Thus, tandem constructs encoded by a recombinant nucleic acid include sequences coding for expression of a donor fluorescent protein moiety, an acceptor fluorescent protein moiety and a peptide linker moiety. The elements are selected so that upon expression into a fusion protein, the donor and acceptor moieties exhibit FRET when the donor moiety is excited.

The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify the tandem construct fusion protein. *E. coli* is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

A primary advantage of tandem construct fusion proteins is that they are prepared by normal protein biosynthesis, thus completely avoiding organic synthesis and the requirement for customized unnatural amino acid analogs. The constructs can be expressed in *E. coli* in large scale for in vitro assays. Purification from bacteria is simplified when the sequences include polyhistidine tags for one-step purification by nickel-chelate chromatography. Alternatively, the substrates can be expressed directly in a desired host cell for assays in situ, which is particularly advantageous if the proteases of interest are membrane-bound or regulated in a complex fashion or not yet abundant as purified stable enzymes. No other generalizable method for continuous nondestructive assay of protease activity in living cells or organisms presently exists.

B. Non-Recombinant Coupling Methods

Fluorescent proteins can be attached through non-recombinant means. In one embodiment, the moieties are attached to a linker by chemical means. This is preferred if the linker moiety is not a peptide. In this case, the linker moiety can comprise a cross-linker moiety. A number of cross-linkers are well known in the art, including homo- or hetero-bifunctional cross-linkers, such as BMH, SPDP, etc. In general, the linker should have a length so as to separate the moieties by about 10 Å to about 100 Å. This is more critical than the particular chemical composition of the linker. Chemical methods for specifically linking molecules to the amino- or carboxy-terminus of a protein are reviewed by R. E. Offord, "Chemical Approaches to Protein Engineering," in *Protein Engineering—A Practical Approach,* (1992) A. R. Rees, M. Sternberg and R. Wetzel, eds., Oxford University Press.

When the protein moieties are to be chemically coupled, fluorescent proteins can be isolated from natural sources by means known in the art. One method involves purifying the proteins to electrophoretic homogeneity. Also, J. R. Deschamps et al. describe a method of purifying recombinant Aequorea GFP in *Protein Expression and Purification,* (1995) 6:555–558.

In another embodiment, the moieties are coupled by attaching each to a nucleic acid molecule. The nucleic acids have sequences of sufficient length and areas of sufficient complementarity to allow hybridization between them, thereby linking the moieties through hydrogen bonds. When the linker contains the sequence of a restriction site, this embodiment allows one to assay for the presence of restriction enzymes by monitoring FRET after the nucleic acid is cleaved and the moieties physically separate.

In another embodiment, the moieties are coupled by attaching each to a polypeptide pair capable of bonding through dimerization. For example, the peptide can include sequences that form a leucine zipper, shown to enable dimerization of a protein to which it was attached. See A. Blondel et al., "Engineering the quaternary structure of an exported protein with a leucine zipper," *Protein Engineering* (1991) 4:457–461. The linker containing the leucine zipper in the Blondel et al. article had the sequence: IQRMKQLED KVEELLSKNY HLENEVARLK KLVGER (SEQ ID NO:17). In another embodiment, a peptide linker moiety can comprise the sequence SKVILF (SEQ OID NO:18), which also is capable of dimerization. See WO 94/28173.

C. Alternative Fluorescent Protein Constructs

This invention also contemplates tandem constructs possessing a single fluorescent protein moiety that functions as donor or acceptor and a non-protein compound fluorescent moiety that functions as donor or quencher. In one embodiment, the construct comprises a donor fluorescent protein moiety, a non-protein compound acceptor fluorescent moiety and a linker moiety that couples the donor and acceptor moieties. Alternatively, a tandem construct can comprise a non-protein compound donor fluorescent moiety, an acceptor fluorescent protein moiety and a linker moiety that couples the donor and acceptor moieties. Non-protein compound fluorescent donor moieties of particular interest include coumarins and fluoresceins; particular quenchers of interest include fluoresceins, rhodols, rhodamines and azo dyes. Acceptable fluorescent dyes are described, for example, in U.S. application Ser. No. 08/407,544, filed Mar. 20, 1995 (allowed, but yet to issue). The donor and acceptor moieties of these constructs are chosen with many of the same considerations for FRET as for tandem fluorescent protein constructs having two fluorescent protein moieties.

III. ENZYMATIC ASSAYS USING TANDEM FLUORESCENT PROTEIN CONSTRUCTS

Tandem fluorescent protein constructs are useful in enzymatic assays. These assays take advantage of the fact that cleavage of the linker moiety and separation of the fluorescent moieties results in a measurable change in FRET. Methods for determining whether a sample has activity of an enzyme involve contacting the sample with a tandem fluorescent protein construct in which the linker moiety that couples the donor and acceptor moieties contains a cleavage recognition site specific for the enzyme. Then the donor moiety is excited with light in its excitation spectrum. If the linker moiety is cleaved, the donor and acceptor are free to drift apart, increasing the distance between the donor and acceptor and preventing FRET. Then, the degree of FRET in the sample is determined. A degree of FRET that is lower than the amount expected in a sample in which the tandem construct is not cleaved indicates that the enzyme is present.

The amount of activity of an enzyme in a sample can be determined by determining the degree of FRET in the sample at a first and second time after contact between the sample and the tandem construct, determining the difference in the degree of FRET. The amount of enzyme in the sample can be calculated as a function of the difference in the degree of FRET using appropriate standards. The faster or larger the loss of FRET, the more enzyme activity must have been present in the sample.

The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor.

For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution.

Fluorescence in a sample is measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., *Principles of Fluorescence Spectroscopy,* New York:Plenum Press (1983); Herman, B., Resonance energy transfer microscopy, in: *Fluorescence Microscopy of Living Cells in Culture, Part B, Methods in Cell Biology,* vol. 30, ed. Taylor, D. L. & Wang, Y.-L., San Diego: Academic Press (1989), pp. 219–243; Turro, N.J., *Modern Molecular Photochemistry,* Menlo Park: Benjamin/Cummings Publishing Col, Inc. (1978), pp. 296–361.

Enzymatic assays also can be performed on living cells in vivo, or from samples derived from organisms transfected to express the tandem construct. Because tandem construct fusion proteins can be expressed recombinantly inside a cell, the amount of enzyme activity in the cell or organism of which it is a part can be determined by determining changes in fluorescence of cells or samples from the organism.

In one embodiment, a cell is transiently or stably transfected with an expression vector encoding a tandem fluorescent protein construct containing a linker moiety that is specifically cleaved by the enzyme to be assayed. This expression vector optionally includes controlling nucleotide sequences such as promotor or enhancing elements. The enzyme to be assayed may either be intrinsic to the cell or may be introduced by stable transfection or transient co-transfection with another expression vector encoding the enzyme and optionally including controlling nucleotide sequences such as promoter or enhancer elements. The fluorescent protein construct and the enzyme preferably are expressed in the same cellular compartment so that they have more opportunity to come into contact.

If the cell does not possess enzyme activity, the efficiency of FRET in the cell is high, and the fluorescence characteristics of the cell reflect this efficiency. If the cell possesses a high degree of enzyme activity, most of the tandem construct expressed by the cell will be cleaved. In this case, the efficiency of FRET is low, reflecting a large amount or high efficiency of the cleavage enzyme relative to the rate of synthesis of the tandem fluorescent protein construct. If the level of enzyme activity in the cell is such that an equilibrium is reached between expression and cleavage of the tandem construct, the fluorescence characteristics will reflect this equilibrium level. In one aspect, this method can be used to compare mutant cells to identify which ones possess greater or less enzymatic activity. Such cells can be sorted by a fluorescent cell sorter based on fluorescence.

A contemplated variation of the above assay is to use the controlling nucleotide sequences to produce a sudden increase in the expression of either the tandem fluorescent protein construct or the enzyme being assayed, e.g., by inducing expression of the construct. The efficiency of FRET is monitored at one or more time intervals after the onset of increased expression. A low efficiency or rapid decline of FRET reflects a large amount or high efficiency of the cleavage enzyme. This kinetic determination has the advantage of minimizing any dependency of the assay on the rates of degradation or loss of the fluorescent protein moieties.

Libraries of host cells expressing tandem fluorescent protein candidate substrates are useful in identifying linker sequences that can be cleaved by a target protease. In general, one begins with a library of recombinant host cells, each of which expresses a different fluorescent protein candidate substrate. Each cell is expanded into a clonal population that is genetically homogeneous. The method consists of measuring FRET from each clonal population before and at least one specified time after a known change in intracellular protease activity. This could be achieved using a fluorimeter, a 96 well plate reader, or by FACS (fluorescence Activated Cell Sorting) anlysis and sorting. This change in protease activity could be produced by transfection with a gene encoding the protease, or infection of a cell by a virus, or induction of protease gene expression using expression control elements, or by any condition that post-translationally modulates the activity of a protease that has already been expressed. An example of the latter is the activation of Calpain 1 by increases in intracellular calcium. The nucleic acids from cells exhibiting a change in FRET can be isolated for example by PCR amplification, and the linker sequences that could be cleaved by the protease identified by sequencing. The results from these studies could used as the basis for the generation of more targeted libraries to identify optimal cleavage motifs through repeated rounds of analysis and selection of clones exhibiting the largest and most rapid changes in FRET in the presence, but not the absence of the protease.

In another embodiment, the vector may be incorporated into an entire organism by standard transgenic or gene replacement techniques. An expression vector capable of expressing the enzyme optionally may be incorporated into the entire organism by standard transgenic or gene replacement techniques. Then, a sample from the organism containing the tandem construct or the cleaved moieties is tested. For example, cell or tissue homogenates, individual cells, or samples of body fluids, such as blood, can be tested.

The enzymatic assays of the invention can be used in drug screening assays to identify compounds that alter the activity of an enzyme. In one embodiment, the assay is performed on a sample in vitro containing the enzyme. A sample containing a known amount of enzyme is mixed with a tandem construct of the invention and with a test compound. The amount of the enzyme activity in the sample is then determined as above, e.g., by determining the degree of fluorescence at a first and second time after contact between the sample, the tandem construct and the compound. Then the amount of activity per mole of enzyme in the presence of the test compound is compared with the activity per mole of enzyme in the absence of the test compound. A difference indicates that the test compound alters the activity of the enzyme.

In another embodiment, the ability of a compound to alter enzyme activity in vivo is determined. In an in vivo assay, cells transfected with a expression vector encoding a tandem construct of the invention are exposed to different amounts of the test compound, and the effect on fluorescence in each cell can be determined. Typically, the difference is calibrated against standard measurements to yield an absolute amount of enzyme activity. A test compound that inhibits or blocks the expression of the enzyme can be detected by increased FRET in treated cells compared to untreated controls.

The following examples are offered by way of illustration, not by way of limitation.

EXAMPLES

Example 1

Construction of Tandem Fluorescent Protein Constructs

Mutant Green Fluorescent Proteins were created as follows. Random mutagenesis of the Aequorea green fluorescent protein (FIG. 1) was performed by increasing the error rate of the PCR with 0.1 mM $MnCl_2$ and unbalanced nucleotide concentrations. The templates used for PCR encoded the GFP mutants S65T, Y66H and Y66W. They had been cloned into the BamH1 site of the expression vector PRSETB (Invitrogen), which includes a T7 promoter and a polyhistidine tag. The GFP coding region (shown in bold) was flanked by the following 5' and 3' sequences: 5'-G GAT CCC CCC GCT GAA TTC ATG (SEQ ID NO:19) . . . AAA TAA TAA GGA TCC (SEQ ID NO:20) -3'. The 5' primer for the mutagenic PCR was the T7 primer matching the vector sequence; the 3' primer was 5'-GGT AAG CTT TTA TTT GTA TAG TTC ATC CAT GCC-3' (SEQ ID NO:21), specific for the 3' end of GFP, creating a HindIII restriction site next to the stop codon.

Amplification was over 25 cycles (1 min at 94° C., 1 min 52° C., 1 min 72° C.) using the AmpliTaq polymerase from Perkin Elmer). Four separate reactions were run in which the concentration of a different nucleotide was lowered from 200 μM to 50 μM. The PCR products were combined, digested with BamHI and HindIII and ligated to the pRSETB cut with BamHI and HindIII. The ligation mixture was dialyzed against water, dried and subsequently transformed into the bacterial strain BL21(DE3) by electroporation (50 μl electrocompetent cells in 0.1 cm cuvettes, 1900 V, 200 ohm, 25 μF). Colonies on agar were visually screened for brightness as previously described. R. Heim et al., "Wavelength mutations and post-translational autooxidation of green fluorescent protein," *Proc Natl Acad Sci USA* 1994, 91:12501–12504. On the order of 7000 colonies were examined in each successful round of mutagenesis, which is not claimed to be exhaustive. The selected clones were sequenced with the Sequenase version 2.0 kit from U.S. Biochemical.

A nucleic acid sequence encoding a tandem GFP-BFP construct fusion protein was produced as follows. The DNA of the GFP mutant S65C (Heim R, Cubitt A B, Tsien R Y, "Improved green fluorescence," *Nature* 1995, 373:663–664) was amplified by PCR (1 cycle 3 min 94° C., 2 min 33° C., 2 min 72° C.; 20 cycles 1 min 94° C., 1 min 44° C., 1 min 72° C.) with Pfu polymerase (Stratagene) using the primers 5'-AGA AAG GCT AGC AAA GGA GAA GAA C-3' (SEQ ID NO:22) and 5'-T CAG TCT AGA TTT GTA TAG TTC ATC-3' (SEQ ID NO:23) to create a NheI site and a (NheI compatible) XbaI site and to eliminate the GFP stop codon. The restricted product was cloned in-frame into the NheI site of the construct pRSETB-Y66H/Y145F, between a polyhistidine tag and an enterokinase cleavage site. When translated this fusion gives the following sequence: MRGSHHHHHH GMA (SEQ ID NO:24)—(S2 . . . GFP:S65C . . . K238 "S65C")—SSMTGGQQMG RDLYDDDDKD PPAEF (SEQ ID NO:25)—(GFP:Y66H/Y145F "P4-3") The linker moiety includes cleavage recognition sites for many proteases, including trypsin, enterokinase and calpain:

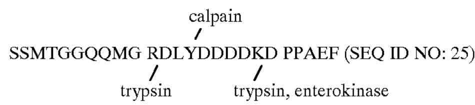

Several other constructs were constructed and tested using the same linker moiety. One of these has the structure S65C—linker—P4. Another had the structure S65C—linker—W7. A third construct had the structure S65T—linker—W7. A fourth construct had the structure P4-3—linker—W7.

Cultures with freshly transformed *E. coli* cells were grown at 37° C. to an optical density of 0.8 at 600 nm, then induced with 0.4 mM isopropylthiogalactoside overnight at room temperature. Expression levels were roughly equivalent between mutants and are typical for the T7 expression system used. Cells were washed in PBS pH 7.4, resuspended in 50 mM Tris pH 8.0, 300 mM NaCl and lysed in a French press. The polyhistidine-tagged GFP proteins were purified from cleared lysates on nickel-chelate columns (Qiagen) using 100 mM imidazole in the above buffer to elute the protein. Samples used for proteolytic experiments were further purified by MonoQ FPLC to remove monomeric GFP. Protein concentrations were estimated with bicinchoninic acid (BCA kit from Pierce) using bovine serum albumin as a standard.

Example 2

Cleavage Measurements

Proteolytic cleavage of 10 μg of the various GFP-BFP fusion proteins were performed in 500 μl PBS pH 7.4 with 0.1 μg trypsin (Sigma, grade III) and emission spectra were recorded at different time intervals. Analogous cleavage experiments were done also with enterokinase (Sigma) and calpain.

Excitation spectra were obtained by collecting emission at the respective peak wavelengths and were corrected by a Rhodamine B quantum counter. Emission spectra were likewise measured at the respective excitation peaks and were corrected using factors from the fluorometer manufacturer (Spex Industries, Edison, N.J.). In cleavage experiments emission spectra were recorded at excitation 368 nm or at 432 nm. For measuring molar extinction coefficients, 20 to 30 μg of protein were used in 1 ml of PBS pH 7.4. The extinction coefficients in TABLE I necessarily assume that the protein is homogeneous and properly folded; if this assumption is incorrect, the real extinction coefficients could be yet higher. Quantum yields of wild-type GFP, S65T, and P4-1 mutants were estimated by comparison with fluorescein in 0.1 N NaOH as a standard of quantum yield 0.91. J. N. Miller, ed., *Standards in Fluorescence Spectrometry,* New York: Chapman and Hall (1981). Mutants P4 and P4-3 were likewise compared to 9-aminoacridine in water (quantum yield 0.98). W2 and W7 were compared to both standards, which gave concordant results.

Excited at 368 nm, the uncleaved S65C—linker—P4-3 construct emitted bright green light that gradually dimmed upon cleavage of the linker to separate the protein domains. As the cleavage by trypsin progressed (0, 2, 5, 10, and 47 min), more blue light was emitted. There was no further change after 47 minutes.

Figure 3:
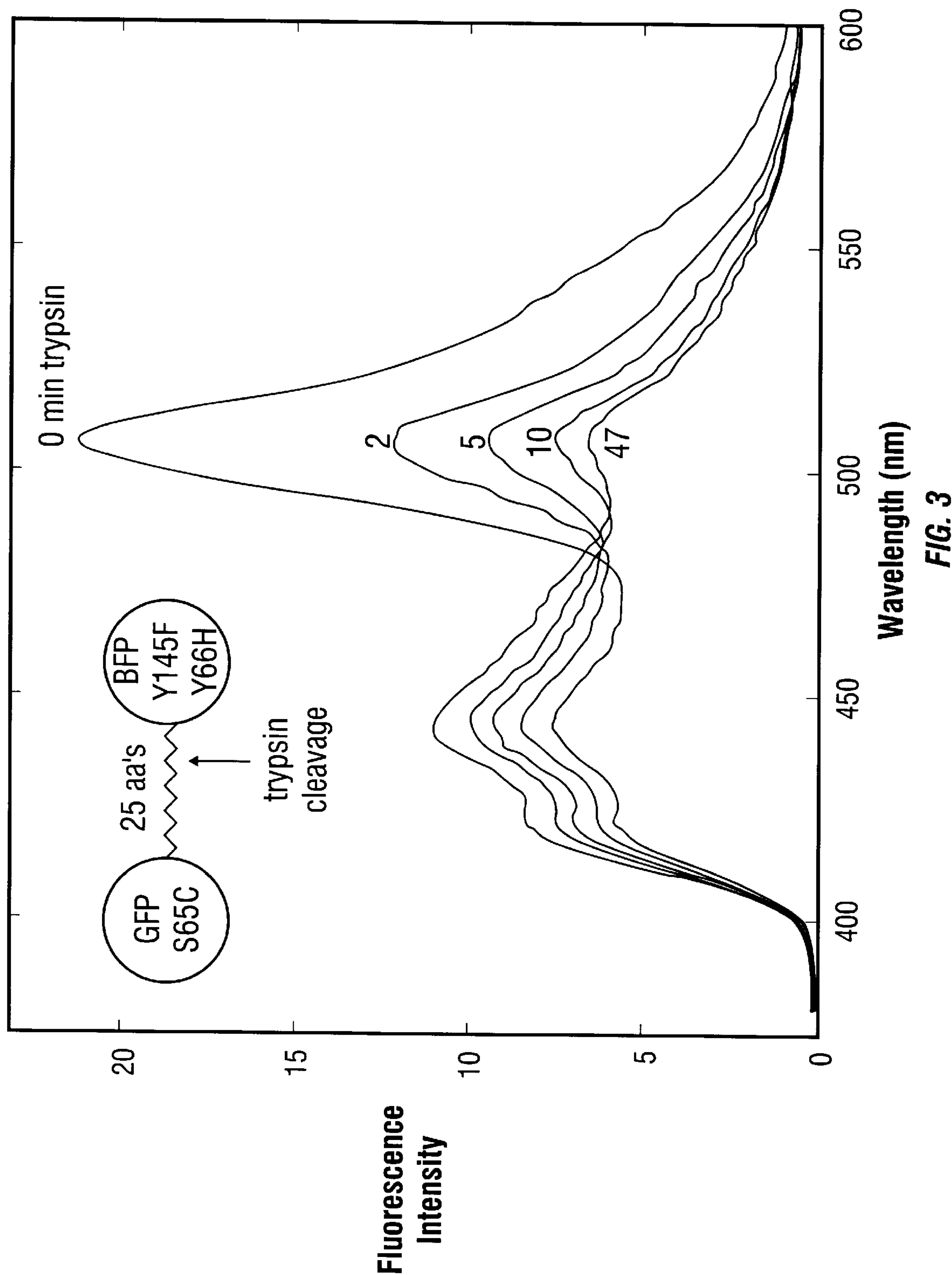
FIG. 3 depicts fluorescence emission spectra of a composition containing a tandem S65C—linker—P4-3 fluorescent protein construct excited at 368 nm after exposure to trypsin for 0, 2, 5, 10 and 47 minutes.

The emission spectrum of the intact fusion protein (FIG. 3) shows that FRET is fairly efficient, because UV excitation causes substantial green emission from the acceptor S65C. After proteolytic cleavage of the spacer, which permits the two domains to diffuse apart, the green emission almost completely disappears, whereas the blue emission from the Y66H/Y145F is enhanced because its excited state is no longer being quenched by the acceptor. Control experiments with the same proteolytic conditions applied to either GFP mutant alone showed no effect, arguing that the GFP domains per se are resistant to proteolysis, as is known to be the case for the native protein. W. W. Ward et al., "Spectral perturbations of the Aequorea green-fluorescent protein," *Photochem. Photobiol.* (1982) 35:803–808.

Figure 4:
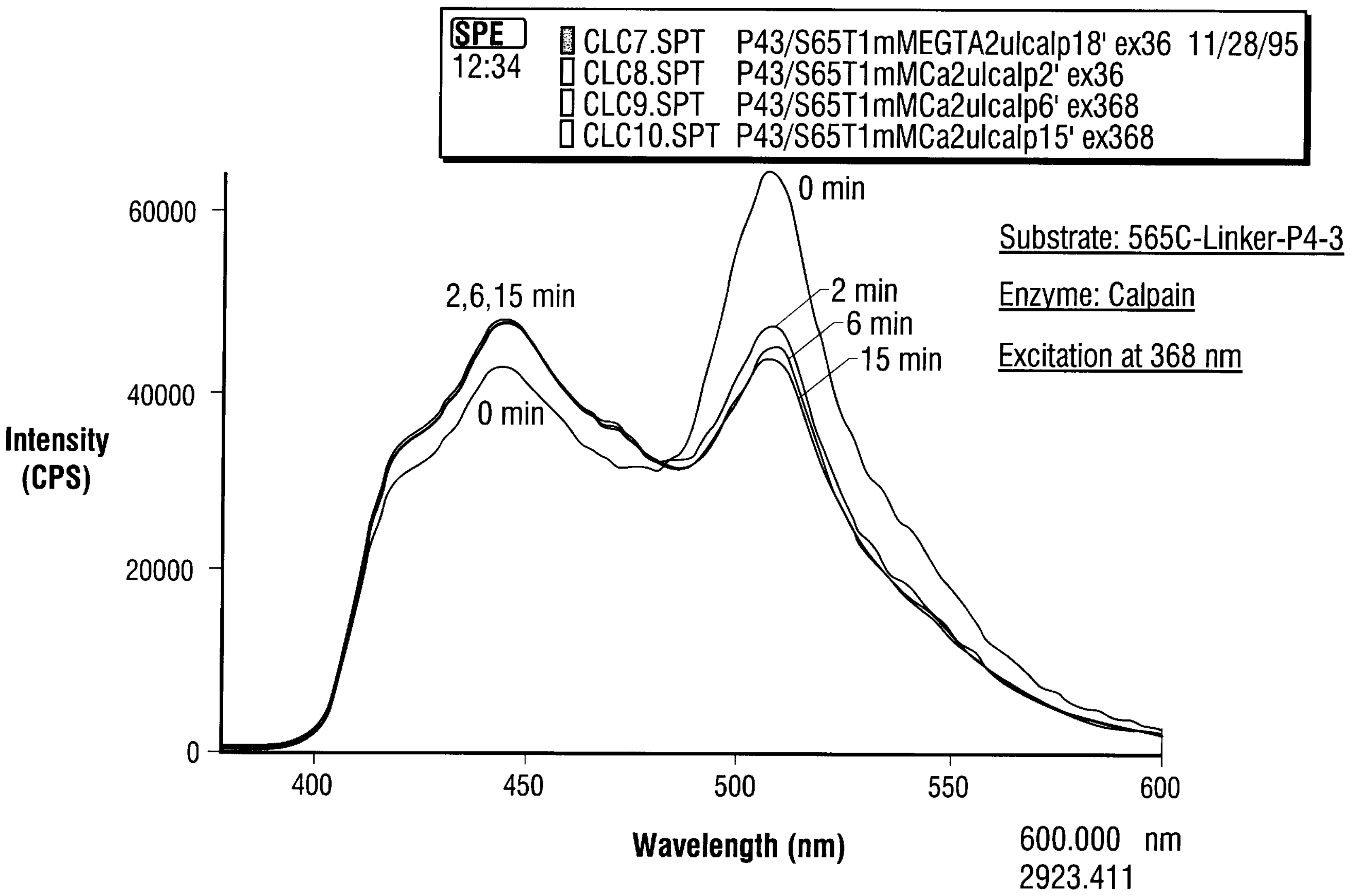
FIG. 4 depicts fluorescence emission spectra intensity of a composition containing a tandem S65C—linker—P4-3 fluorescent protein construct excited at 368 nm after exposure to calpain for 0, 2, 6 and 15 minutes.

Similar result were obtained when the S65C—linker—P4-3 fusion construct was cleaved with calpain and excited at 368 nm. (See FIG. 4.)

Figure 5:
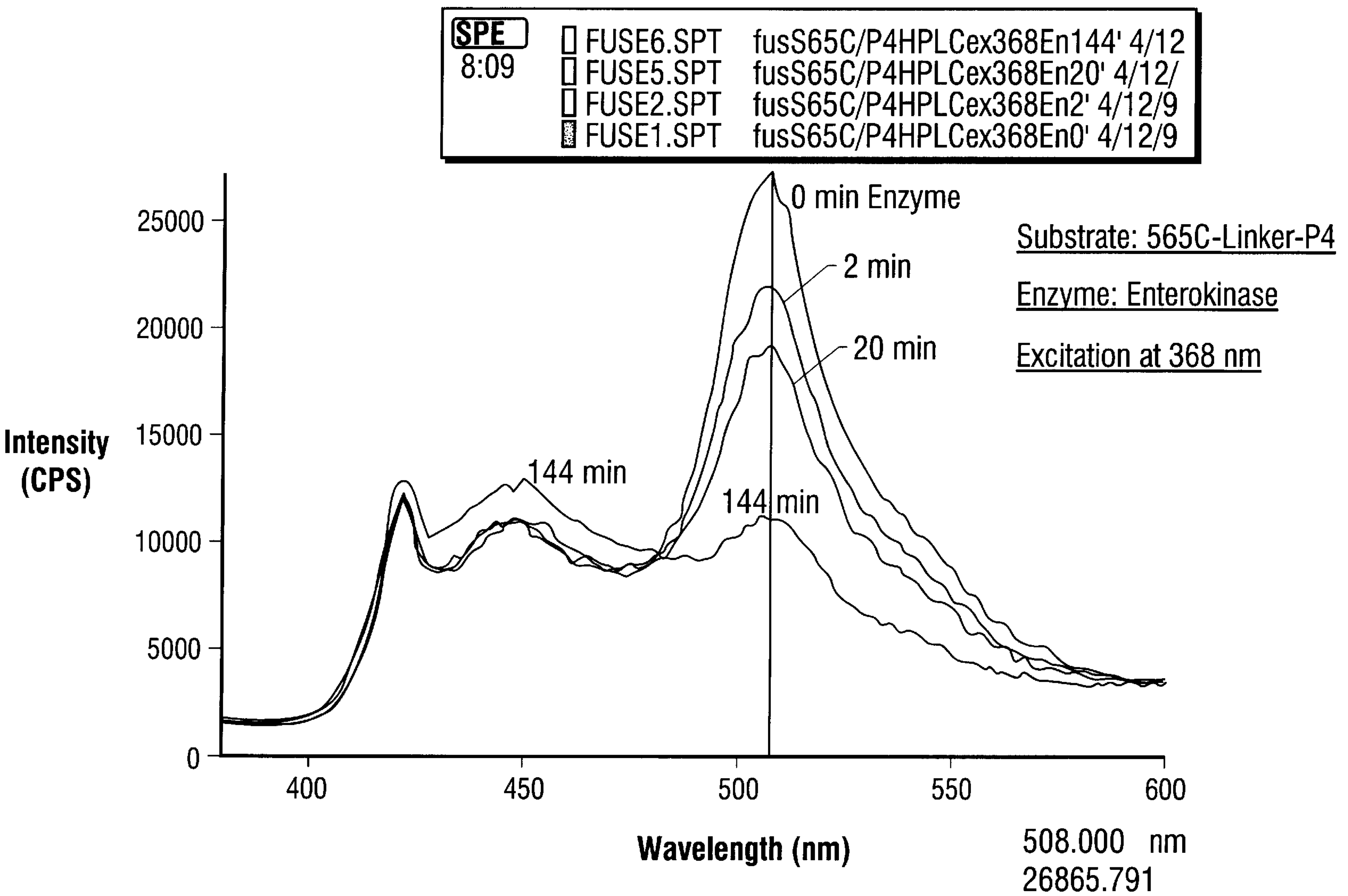
FIG. 5 depicts fluorescence emission spectra of a composition containing a tandem S65C—linker—P4 fluorescent protein construct excited at 368 nm after exposure to enterokinase for 0, 2, 20 and 144 minutes.

The tandem construct S65C—linker—P4 was exposed to enterokinase and excited at 368 nm. FRET diminished over time, demonstrating that one could detect cleavage of the linker by enterokinase. (See FIG. 5.)

Figure 6:
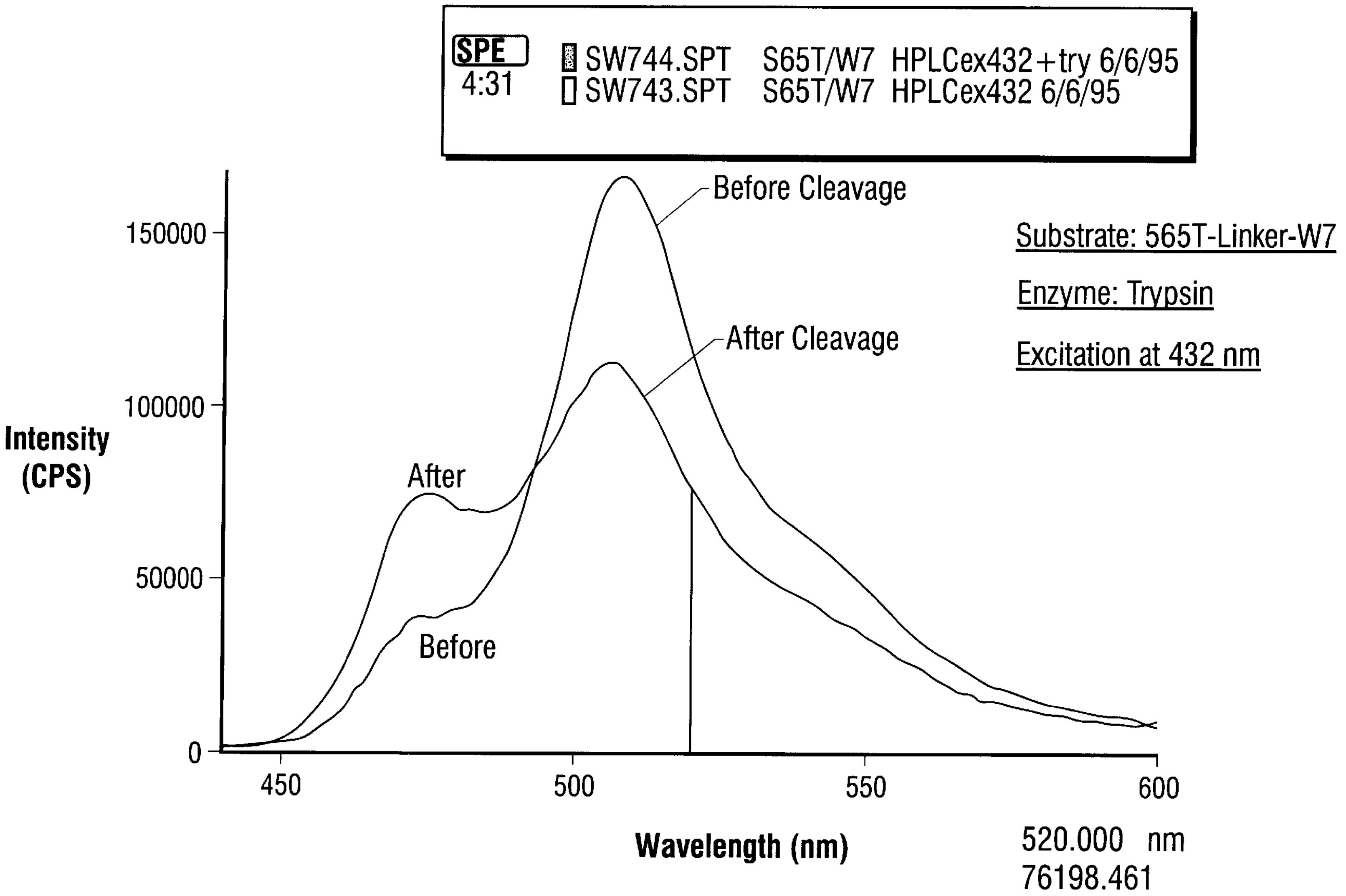
FIG. 6 depicts fluorescence emission spectra of a composition containing a tandem S65T—linker—W7 fluorescent protein construct excited at 432 nm before and after exposure to trypsin.

The tandem construct S65T—linker—W7 was exposed to trypsin and excited at 432 nm. Cleavage of the linker and separation of the moieties was detectable as a decrease in FRET over time. (See FIG. 6.)

Figure 7:
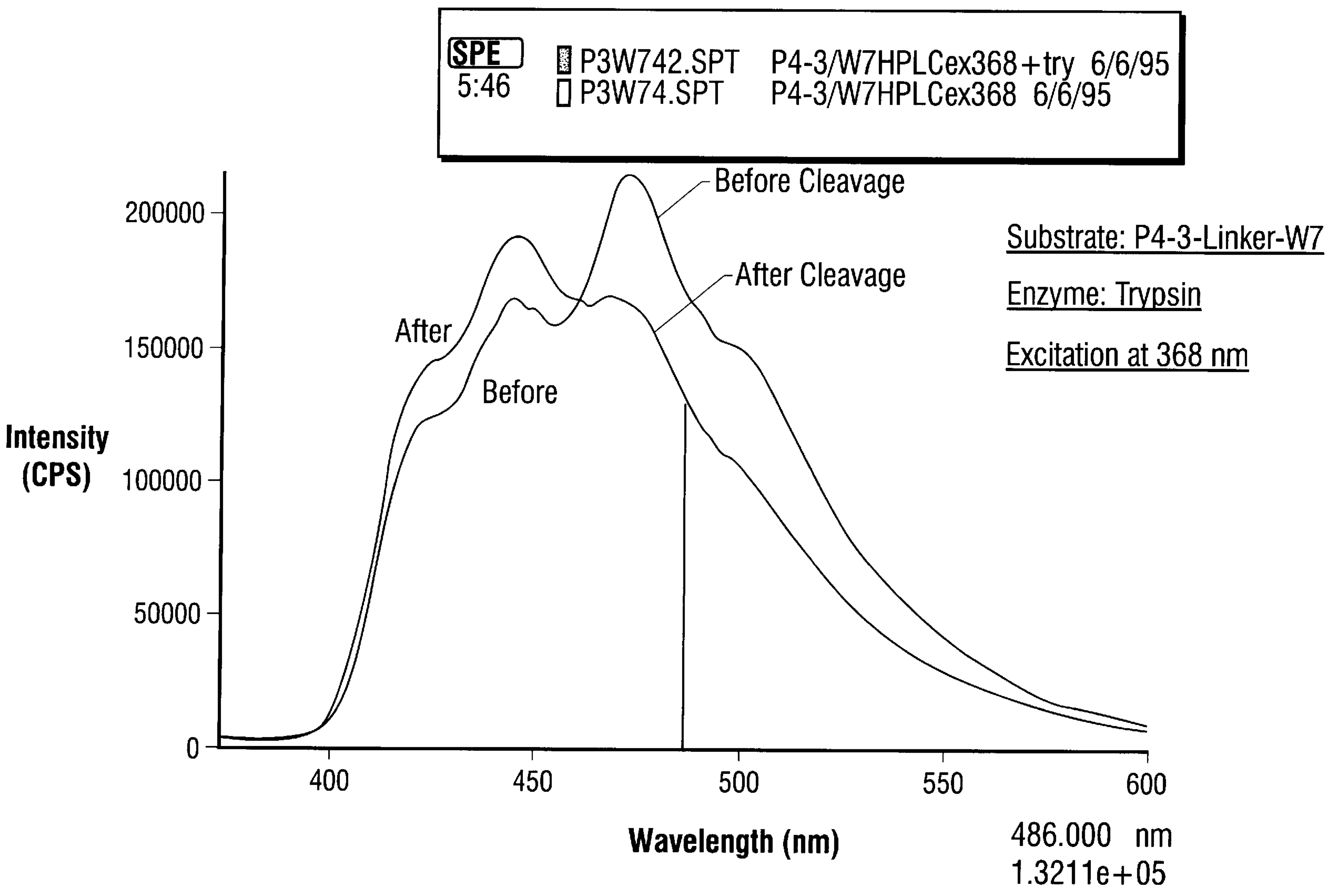
FIG. 7 depicts fluorescence emission spectra of a composition containing a tandem P4-3—linker—W7 fluorescent protein construct excited at 368 nm before and after exposure to trypsin.

The tandem construct P4-3—linker—W7 was exposed to trypsin and excited at 368 nm. FIG. 7. demonstrates the change in FRET resulting from cleavage.

Figure 8:
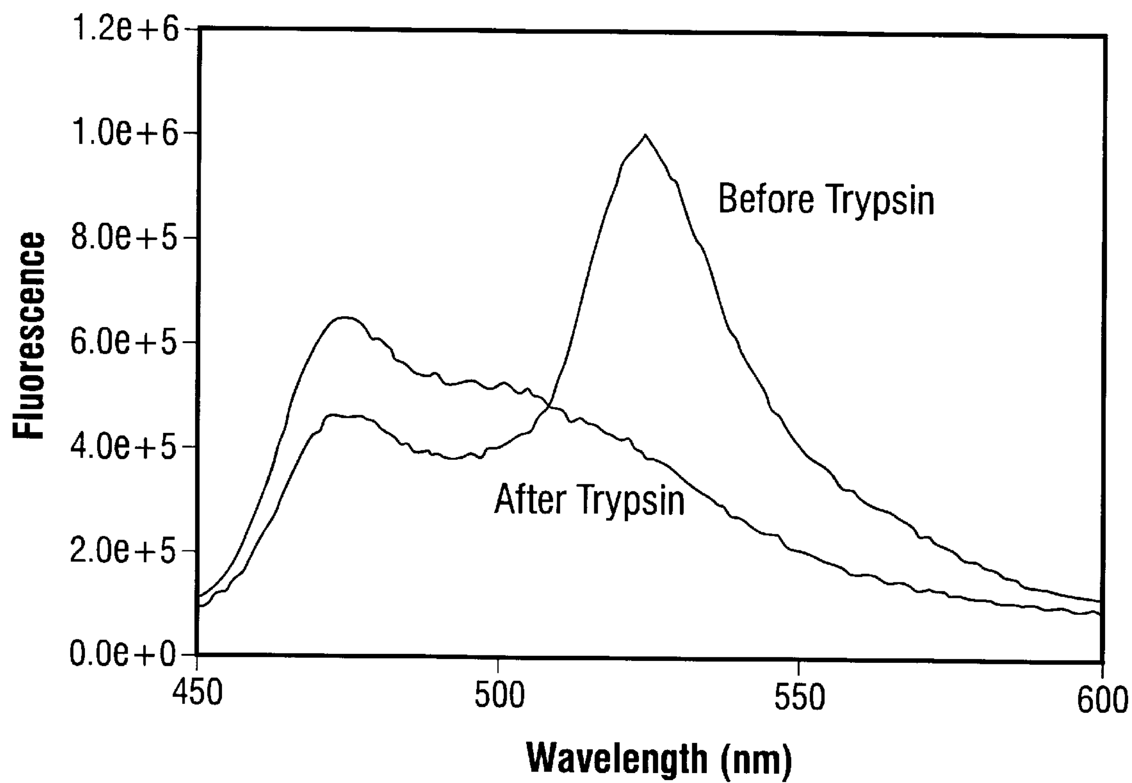
FIG. 8 depicts fluorescence emission spectra of a composition containing a tandem W1B—linker—10c fluorescent protein construct excited at 433 nm before and after exposure to trypsin.

The tandem construct W1B—linker—10c was exposed to trypsin and excited at 433 nm. FIG. 8. demonstrates the change in FRET resulting from cleavage.

Figure 9:
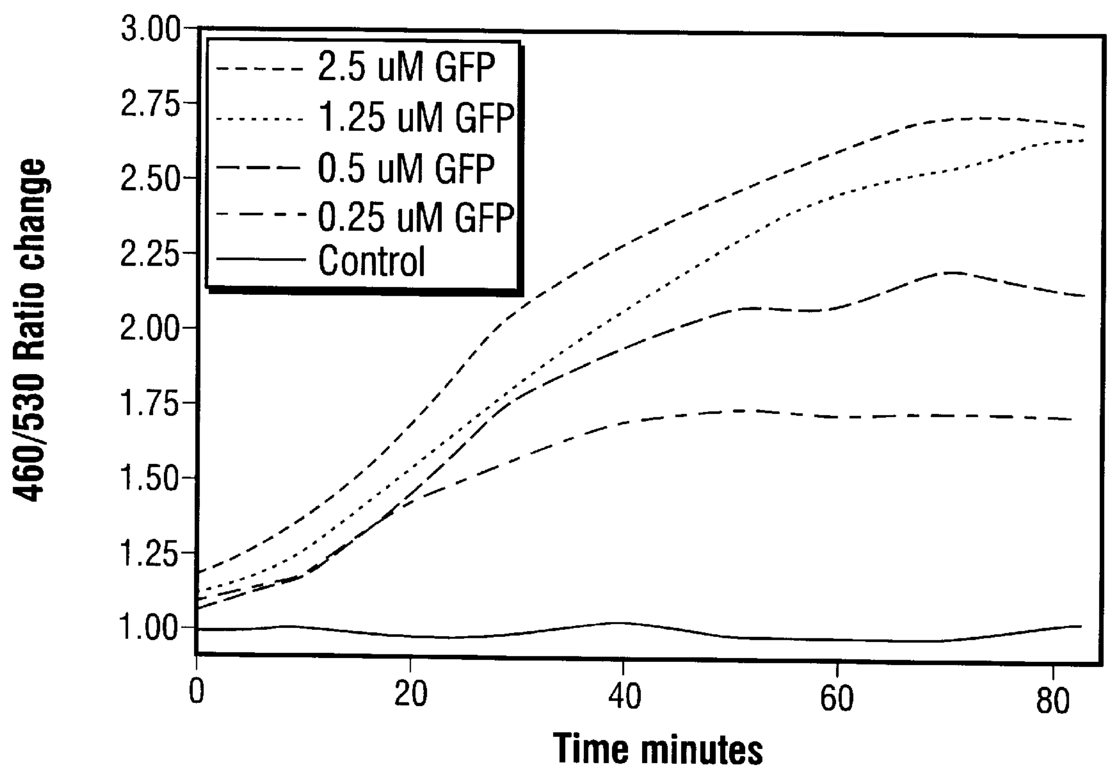
FIG. 9 depicts the time course of fluorescent ratio changes upon cleavage of a composition containing the tandem W1B—linker—10c fluorescent protein construct measured at different protein concentrations after exposure to trypsin measured in a fluorescent 96 well plate reader.

FIG. 9 depicts fluorescent ratio changes upon cleavage of a composition containing the tandem construct W1B—linker—10c fluorescent construct at different protein concentrations after exposure to trypsin measured in a fluorescent 96 well microtitre plate reader (a CytoFluor II Series 4000 Perseptive Biosystems. Microtitre wells were excited with light at 395+/−25 nm, and the emitted light measured at 460+/−20 nm and 530+/−15 nm using appriopriate excitation and emission filter sets.

These different tandem fluorescent protein constructs demonstrate that fluorescence resonance energy transfer can monitor the distance between fluorescent protein domains. Disruption of FRET between man-made chromophores in a short synthetic peptide has been used before to assay proteases (G. A. Krafft et al., "Synthetic approaches to continuous assays of retroviral proteases," *Methods Enzymol.* (1994) 241:70–86; C. G. Knight, "Fluorimetric assays of proteolytic enzymes," *Methods Enzymol.* (1995) 248:18–34), but use of fluorescent proteins as the fluorophores gives the unique possibility of replacing organic synthesis by molecular biology and monitoring proteases in situ in living cells and organisms. FRET is also one of the few methods for imaging dynamic non-covalent protein-protein associations in situ.

The present invention provides novel tandem fluorescent protein constructs and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A tandem fluorescent protein construct, comprising:

a donor fluorescent protein moiety, an acceptor fluorescent protein moiety, and a peptide linker moiety coupling said donor fluorescent protein moiety and said acceptor fluorescent protein moiety, wherein cyclized amino acids of said donor fluorescent protein moiety emit light characteristic of said donor fluorescent protein moiety, further wherein said donor fluorescent protein moiety and said acceptor fluorescent protein moiety exhibit fluorescence resonance energy transfer when said donor fluorescent protein moiety is excited, and said linker moiety does not substantially emit light to excite said donor fluorescent protein moiety.

2. The tandem fluorescent protein construct of claim 1, wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212.

3. The tandem fluorescent protein construct of claim 1, wherein both of said donor fluorescent protein moiety and said acceptor fluorescent protein moiety are an Aequorea-related fluorescent protein moiety.

4. The tandem fluorescent protein construct of claim 3, wherein said mutation is selected from the group consisting of F64L, S65G, S65T, Y66F, Y66H, Y66W, V68L, S72A, Y145F, N146I, N149K, M153T, V163A, I167T, T203I, T203Y, and N212K.

5. The tandem fluorescent protein construct of claim 4, wherein said mutation is selected for 10c, W1B, Emerald, and Sapphire.

6. The tandem fluorescent protein construct of claim 5, wherein said donor fluorescent protein moiety is P4-3, Sapphire, W7, or Y66H and said acceptor protein fluorescent moiety is W7, Topaz, S65T, or S65C, with the proviso that when said donor fluorescent protein moiety is P4-3, then said acceptor fluorescent protein moiety is not S65T or S65C and when said donor fluorescent protein moiety is W7, then said acceptor fluorescent moiety is not S65T.

7. The tandem fluorescent protein construct of claim 1, wherein said linker moiety comprises a cleavage recognition site for an enzyme.

8. The tandem fluorescent protein construct of claim 7, wherein said linker moiety is a peptide moiety.

9. The tandem fluorescent protein construct of claim 8, wherein said donor fluorescent protein moiety, said acceptor fluorescent protein moiety, and said linker moiety comprise a single polypeptide.

10. The tandem fluorescent protein construct of claim 9, wherein said linker moiety comprises between about 5 and 50 amino acids.

11. The tandem fluorescent protein construct of claim 10, wherein said linker moiety comprises between about 10 and 30 amino acids.

12. The tandem fluorescent protein construct of claim 9, wherein said linker moiety comprises a cleavage recognition site for an enzyme selected from the group consisting of trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin D and a kininogenase.

13. The tandem fluorescent protein construct of claim 10, wherein said donor fluorescent protein moiety is positioned at the amino terminus of the polypeptide relative to said acceptor fluorescent protein moiety.

14. The tandem fluorescent protein construct of claim 1, wherein said peptide linker moiety is of a length and orientation that allows fluorescent energy transfer between said donor fluorescent protein moiety and said acceptor fluorescent protein moiety.

15. The tandem fluorescent protein construct of claim 7, comprising a cleavage recognition site for beta-lactamase.

16. The tandem fluorescent protein construct of claim 11, wherein said linker moiety comprises a protease recognition site.

17. A recombinant nucleic acid encoding for the expression of a functional tandem fluorescent protein construct, said tandem fluorescent protein construct comprising:

a donor fluorescent protein moiety, an acceptor fluorescent protein moiety, and a peptide linker moiety coupling said donor fluorescent protein moiety and said acceptor fluorescent protein moiety, wherein said donor fluorescent protein moiety and said acceptor fluorescent protein moiety exhibit fluorescence resonance energy transfer when said donor fluorescent protein moiety is excited, and said peptide linker moiety does not substantially emit light to excite said donor fluorescent protein moiety, further wherein said peptide linker moiety comprises a cleavage recognition site for a protease.

18. The recombinant nucleic acid of claim 17, wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212.

19. The recombinant nucleic acid of claim 7, wherein said peptide linker moiety is of a length and orientation that allows fluorescent resonance energy transfer between said donor fluorescent protein moiety and said acceptor fluorescent protein moiety.

20. An expression vector, comprising: an expression control sequence operatively linked to a sequence coding for the expression of a functional tandem fluorescent protein construct, said tandem fluorescent protein construct comprising:

a donor fluorescent protein moiety, an acceptor fluorescent protein moiety, and a peptide linker moiety coupling said donor fluorescent protein moiety and said acceptor fluorescent protein moiety, wherein said donor fluorescent protein moiety and said acceptor fluorescent protein moiety exhibit fluorescence resonance energy transfer when said donor fluorescent protein moiety is excited, and said peptide linker moiety does not substantially emit light to excite said donor fluorescent protein moiety further wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212.

21. A host cell transfected with an expression vector, said expression vector comprising: an expression control sequence operatively linked to a sequence coding for the expression of a functional tandem fluorescent protein construct, said tandem fluorescent protein construct comprising:

a donor fluorescent protein moiety, an acceptor fluorescent protein moiety, and a peptide linker moiety coupling said donor fluorescent protein moiety and said acceptor fluorescent protein moiety, wherein said donor fluorescent protein moiety and said acceptor fluorescent protein moiety exhibit fluorescence resonance energy transfer when said donor fluorescent protein moiety is excited, and said peptide linker moiety does not substantially emit light to excite said donor fluorescent protein moiety, wherein said peptide linker moiety comprises a cleavage recognition site for a protease.

22. The host cell of claim 21, wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212.

23. A method for determining whether a sample contains an enzyme, comprising:

contacting a sample with a tandem fluorescent protein construct, said tandem fluorescent protein construct comprising:

a donor fluorescent protein moiety, an acceptor fluorescent protein moiety, and a linker moiety comprising a cleavage recognition site for an enzyme, coupling said donor fluorescent protein moiety and said acceptor fluorescent protein moiety, wherein cyclized amino acids of said donor fluorescent protein moiety emit light characteristic of said donor fluorescent protein moiety, further wherein said donor fluorescent protein moiety and said acceptor fluorescent protein moiety exhibit fluorescence resonance energy transfer when said donor fluorescent protein moiety is excited, and said linker moiety does not substantially emit light to excite said donor fluorescent protein moiety, further wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212, exciting said donor fluorescent protein moiety, and determining a fluorescence property in said sample, wherein the presence of said enzyme in said sample results in a change in the degree of fluorescence resonance energy transfer.

24. A method for determining the activity of an enzyme in a cell, comprising:

providing a cell that expresses a tandem fluorescent protein construct, said tandem fluorescent protein construct comprising:

a donor fluorescent protein moiety, an acceptor fluorescent protein moiety, and a peptide linker moiety comprising a cleavage recognition amino acid sequence specific for said enzyme coupling said donor fluorescent protein moiety and said acceptor fluorescent protein moiety, wherein cyclized amino acids of said donor fluorescent protein moiety emit light characteristic of said donor fluorescent protein moiety, further wherein said donor fluorescent protein moiety and said acceptor fluorescent protein moiety exhibit fluorescence resonance energy transfer when said donor fluorescent protein moiety is excited, and said linker moiety does not substantially emit light to excite said donor fluorescent protein moiety, further wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212, exciting said donor fluorescent protein moiety, and determining the degree of fluorescence resonance energy transfer in said cell, wherein the presence of said activity in said cell results in a change in the degree of fluorescence resonance energy transfer.

25. A method for determining the amount of activity of an enzyme in a sample from an organism, comprising:

contacting a sample from an organism with a tandem fluorescent protein construct, said construct comprising a donor fluorescent protein moiety, an acceptor fluorescent protein moiety, and a peptide linker moiety comprising a cleavage recognition amino acid sequence specific for said enzyme coupling said donor fluorescent protein moiety and said acceptor fluorescent protein moiety, wherein cyclized amino acids of said donor fluorescent protein moiety emit light characteristic of said donor fluorescent protein moiety, further wherein said donor fluorescent protein moiety and said acceptor fluorescent protein moiety exhibit fluorescence resonance energy transfer when said donor fluorescent protein moiety is excited, and said peptide linker moiety does not substantially emit light to excite said donor fluorescent protein moiety, further wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212, and exciting said donor fluorescent protein moiety, and determining the degree of fluorescence resonance energy transfer in said sample, wherein the presence of said activity in said sample results in a change in the degree of fluorescence resonance energy transfer.

26. A method for determining whether a compound alters the activity of an enzyme, comprising:

contacting a sample containing an enzyme with a compound and a tandem fluorescent protein construct, said tandem fluorescent protein construct comprising:

a donor fluorescent protein moiety, an acceptor fluorescent protein moiety, and a linker moiety coupling said donor fluorescent protein moiety and said acceptor fluorescent protein moiety, wherein cyclized amino acids of said donor fluorescent protein moiety emit light characteristic of said donor fluorescent protein moiety, further wherein said donor fluorescent protein moiety and said acceptor fluorescent protein moiety exhibit fluorescence resonance energy transfer when said donor fluorescent protein moiety is excited, and said linker moiety does not substantially emit light to excite said donor fluorescent protein moiety, further wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212, and exciting said donor fluorescent protein moiety, and determining a fluorescent property of said sample, wherein an activity of said enzyme is determined by a change in the degree of said fluorescent property in the presence and absence of said compound.

27. A method for determining whether a compound alters the activity of an enzyme in a cell, comprising:

providing a first and second cells that express a tandem fluorescent protein construct, said tandem fluorescent protein construct comprising:

a donor fluorescent protein moiety, an acceptor fluorescent protein moiety, and a peptide linker moiety comprising a cleavage recognition amino acid sequence specific for said enzyme coupling said donor fluorescent protein moiety and said acceptor fluorescent protein moiety, wherein cyclized amino acids of said donor fluorescent protein moiety emit light characteristic of said donor fluorescent protein moiety, further wherein said donor fluorescent protein moiety and said acceptor fluorescent protein moiety exhibit fluorescence resonance energy transfer when said donor fluorescent protein moiety is excited, and said peptide linker moiety does not substantially emit light to excite said donor fluorescent protein moiety, and exciting said donor fluorescent protein moiety, contacting said first cell with an amount of said compound, contacting the second cell with a different amount of said compound, further wherein at least one of said donor fluorescent moiety and said acceptor fluorescent protein moiety comprises an Aequorea-related fluorescent protein moiety comprising a mutation at a position selected from the group consisting of F64, S65, Y66, V68, S72, Y145, N146, N149, M153, V163, I167, T203, and N212, and exciting said donor fluorescent protein moiety in said first and second cell, determining the degree of fluorescence resonance energy transfer in said first and second cells, and comparing the degree of fluorescence resonance energy transfer in said first cell and said second cell, wherein a difference in the degree of fluorescence resonance energy transfer in said first cell and said second cell indicates that the compound alters the activity of said enzyme.

* * * * *

SEQUENCE LISTING

```
(1) GENERAL INFORMATION:

   (iii) NUMBER OF SEQUENCES: 25

(2) INFORMATION FOR SEQ ID NO:1:

     (i) SEQUENCE CHARACTERISTICS:
          (A) LENGTH: 716 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..717

    (xi) SEQUENCE DESCRIPTION: SEQ ID NO:1:

ATG AGT AAA GGA GAA GAA CTT TTC ACT GGA GTT GTC CCA ATT CTT GTT       48
Met Ser Lys Gly Glu Glu Leu Phe Thr Gly Val Val Pro Ile Leu Val
  1               5                  10                  15

GAA TTA GAT GGT GAT GTT AAT GGG CAC AAA TTT TCT GTC AGT GGA GAG       96
Glu Leu Asp Gly Asp Val Asn Gly His Lys Phe Ser Val Ser Gly Glu
             20                  25                  30

GGT GAA GGT GAT GCA ACA TAC GGA AAA CTT ACC CTT AAA TTT ATT TGC      144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT TTC      192
Thr Thr Gly Lys Leu Pro Val Pro Trp Pro Thr Leu Val Thr Thr Phe
     50                  55                  60

TCT TAT GGT GTT CAA TGC TTT TCA AGA TAC CCA GAT CAT ATG AAA CGG      240
Ser Tyr Gly Val Gln Cys Phe Ser Arg Tyr Pro Asp His Met Lys Arg
 65                  70                  75                  80

CAT GAC TTT TTC AAG AGT GCC ATG CCC GAA GGT TAT GTA CAG GAA AGA      288
His Asp Phe Phe Lys Ser Ala Met Pro Glu Gly Tyr Val Gln Glu Arg
                 85                  90                  95

ACT ATA TTT TTC AAA GAT GAC GGG AAC TAC AAG ACA CGT GCT GAA GTC      336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT      384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAC AAA TTG GAA TAC AAC      432
Asp Phe Lys Glu Asp Gly Asn Ile Leu Gly His Lys Leu Glu Tyr Asn
```

```
    130                 135                 140

TAT AAC TCA CAC AAT GTA TAC ATC ATG GCA GAC AAA CAA AAG AAT GGA      480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT      528
Ile Lys Val Asn Phe Lys Ile Arg His Asn Ile Glu Asp Gly Ser Val
                165                 170                 175

CAA CTA GCA GAC CAT TAT CAA CAA AAT ACT CCA ATT GGC GAT GGC CCT      576
Gln Leu Ala Asp His Tyr Gln Gln Asn Thr Pro Ile Gly Asp Gly Pro
            180                 185                 190

GTC CTT TTA CCA GAC AAC CAT TAC CTG TCC ACA CAA TCT GCC CTT TCG      624
Val Leu Leu Pro Asp Asn His Tyr Leu Ser Thr Gln Ser Ala Leu Ser
        195                 200                 205

AAA GAT CCC AAC GAA AAG AGA GAC CAC ATG GTC CTT CTT GAG TTT GTA      672
Lys Asp Pro Asn Glu Lys Arg Asp His Met Val Leu Leu Glu Phe Val
    210                 215                 220

ACA GCT GCT GGG ATT ACA CAT GGC ATG GAT GAA CTA TAC AAA TA           716
Thr Ala Ala Gly Ile Thr His Gly Met Asp Glu Leu Tyr Lys
225                 230                 235
```

(2) INFORMATION FOR SEQ ID NO:2:

(i) SEQUENCE CHARACTERISTICS:
(A) LENGTH: 238 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220
```

```
Thr Ala Ala Gly Ile Thr His Gly Met Asp Glu Leu Tyr Lys
225                 230                 235


(2) INFORMATION FOR SEQ ID NO:3:

     (i) SEQUENCE CHARACTERISTICS:
          (A) LENGTH: 8 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:3:

Ser Gln Asn Tyr Pro Ile Val Gly
1               5


(2) INFORMATION FOR SEQ ID NO:4:

     (i) SEQUENCE CHARACTERISTICS:
          (A) LENGTH: 10 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:4:

Lys Ala Arg Val Leu Ala Glu Ala Met Ser
1               5                   10


(2) INFORMATION FOR SEQ ID NO:5:

     (i) SEQUENCE CHARACTERISTICS:
          (A) LENGTH: 10 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:5:

Pro Ser Pro Arg Glu Gly Lys Arg Ser Tyr
1               5                   10


(2) INFORMATION FOR SEQ ID NO:6:

     (i) SEQUENCE CHARACTERISTICS:
          (A) LENGTH: 5 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:6:

Tyr Val Ala Asp Gly
1               5


(2) INFORMATION FOR SEQ ID NO:7:

     (i) SEQUENCE CHARACTERISTICS:
          (A) LENGTH: 8 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:7:
```

```
Met Phe Gly Gly Ala Lys Lys Arg
1               5


(2) INFORMATION FOR SEQ ID NO:8:

     (i) SEQUENCE CHARACTERISTICS:
          (A) LENGTH: 10 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:8:

Gly Val Val Asn Ala Ser Ser Arg Leu Ala
1               5                   10


(2) INFORMATION FOR SEQ ID NO:9:

     (i) SEQUENCE CHARACTERISTICS:
          (A) LENGTH: 9 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:9:

Leu Ile Ala Tyr Leu Lys Lys Ala Thr
1               5


(2) INFORMATION FOR SEQ ID NO:10:

     (i) SEQUENCE CHARACTERISTICS:
          (A) LENGTH: 7 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:10:

Val Lys Met Asp Ala Glu Phe
1               5


(2) INFORMATION FOR SEQ ID NO:11:

     (i) SEQUENCE CHARACTERISTICS:
          (A) LENGTH: 17 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:11:

Phe Leu Ala Glu Gly Gly Gly Val Arg Gly Pro Arg Val Val Glu Arg  Hi
1               5                   10                  15


(2) INFORMATION FOR SEQ ID NO:12:

     (i) SEQUENCE CHARACTERISTICS:
          (A) LENGTH: 13 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:12:
```

```
Asp Arg Val Tyr Ile His Pro Phe His Leu Val Ile His
1               5                   10


(2) INFORMATION FOR SEQ ID NO:13:

     (i) SEQUENCE CHARACTERISTICS:
          (A) LENGTH: 8 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:13:

Lys Pro Ala Leu Phe Phe Arg Leu
1               5


(2) INFORMATION FOR SEQ ID NO:14:

     (i) SEQUENCE CHARACTERISTICS:
          (A) LENGTH: 30 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:14:

Gln Pro Leu Gly Gln Thr Ser Leu Met Lys Arg Pro Pro Gly Phe Ser
1                   5                             10

Pro Phe Arg Ser Val Gln Val Met Lys Thr Gln Glu Gly Ser
            20                  25                  30


(2) INFORMATION FOR SEQ ID NO:15:

     (i) SEQUENCE CHARACTERISTICS:
          (A) LENGTH: 5 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:15:

Gly Gly Gly Gly Ser
1               5


(2) INFORMATION FOR SEQ ID NO:16:

     (i) SEQUENCE CHARACTERISTICS:
          (A) LENGTH: 22 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:16:

Gly Gly Gly Gly Gly Gly Ser Met Phe Gly Gly Ala Lys Lys Arg Ser
1               5                   10                  15

Gly Gly Gly Gly Gly Gly
            20


(2) INFORMATION FOR SEQ ID NO:17:

     (i) SEQUENCE CHARACTERISTICS:
          (A) LENGTH: 35 amino acids
          (B) TYPE: amino acid
          (C) STRANDEDNESS: single
```

(D) TOPOLOGY: linear (ii) MOLECULE TYPE: peptide (xi) SEQUENCE DESCRIPTION: SEQ ID NO:17:

```
Ile Gln Arg Met Lys Gln Leu Glu Asp Lys Val Glu Glu Leu Leu Ser
1               5                   10                  15

Lys Asn Tyr His Leu Glu Asn Glu Val Ala Arg Leu Lys Lys Leu Val
            20                  25                  30

Gly Glu Arg
        35
```

(2) INFORMATION FOR SEQ ID NO:18:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

```
Ser Lys Val Ile Leu Phe
1                   5
```

(2) INFORMATION FOR SEQ ID NO:19:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:19:

```
GGATCCCCCC GCTGAATTCA TG                                              22
```

(2) INFORMATION FOR SEQ ID NO:20:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:20:

```
AAATAATAAG GATCC                                                      15
```

(2) INFORMATION FOR SEQ ID NO:21:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:21:

```
GGTAAGCTTT TATTTGTATA GTTCATCCAT GCC                                  33
```

(2) INFORMATION FOR SEQ ID NO:22:

(i) SEQUENCE CHARACTERISTICS:

-continued

```
        (A) LENGTH: 24 base pairs
        (B) TYPE: nucleic acid
        (C) STRANDEDNESS: single
        (D) TOPOLOGY: linear

   (ii) MOLECULE TYPE: DNA (primer)

   (xi) SEQUENCE DESCRIPTION: SEQ ID NO:22:

AGAAAGGCTA GCAAAGGAGA AGAA                                            24


(2) INFORMATION FOR SEQ ID NO:23:

    (i) SEQUENCE CHARACTERISTICS:
        (A) LENGTH: 25 base pairs
        (B) TYPE: nucleic acid
        (C) STRANDEDNESS: single
        (D) TOPOLOGY: linear

   (ii) MOLECULE TYPE: DNA (primer)

   (xi) SEQUENCE DESCRIPTION: SEQ ID NO:23:

TCAGTCTAGA TTTGTATAGT TCATC                                           25


(2) INFORMATION FOR SEQ ID NO:24:

    (i) SEQUENCE CHARACTERISTICS:
        (A) LENGTH: 10 amino acids
        (B) TYPE: amino acid
        (C) STRANDEDNESS: single
        (D) TOPOLOGY: linear

   (ii) MOLECULE TYPE: peptide

   (xi) SEQUENCE DESCRIPTION: SEQ ID NO:24:

Met Arg Gly Ser His His His His His His
1               5                   10


(2) INFORMATION FOR SEQ ID NO:25:

    (i) SEQUENCE CHARACTERISTICS:
        (A) LENGTH: 25 amino acids
        (B) TYPE: amino acid
        (C) STRANDEDNESS: single
        (D) TOPOLOGY: linear

   (ii) MOLECULE TYPE: peptide

   (xi) SEQUENCE DESCRIPTION: SEQ ID NO:25:

Ser Ser Met Thr Gly Gly Gln Gln Met Gly Arg Asp Leu Tyr Asp Asp
1               5                   10                  15

Asp Asp Lys Asp Pro Pro Ala Glu Phe
            20                  25
```